US012283382B2

(12) United States Patent
Gardina

(10) Patent No.: US 12,283,382 B2
(45) Date of Patent: Apr. 22, 2025

(54) DISTRIBUTED MEDICAL TESTING FRAMEWORK

(71) Applicant: Siromi Gardina, Washington, DC (US)

(72) Inventor: Siromi Gardina, Washington, DC (US)

(*) Notice: Subject to any disclaimer, the term of this patent is extended or adjusted under 35 U.S.C. 154(b) by 449 days.

(21) Appl. No.: 17/576,426

(22) Filed: Jan. 14, 2022

(65) Prior Publication Data

US 2022/0139566 A1 May 5, 2022

Related U.S. Application Data

(63) Continuation-in-part of application No. PCT/US2020/041976, filed on Jul. 14, 2020.

(60) Provisional application No. 62/875,590, filed on Jul. 18, 2019.

(51) Int. Cl.
*H04L 29/06* (2006.01)
*G16H 50/70* (2018.01)
*H04L 9/32* (2006.01)
*H04L 9/00* (2022.01)

(52) U.S. Cl.
CPC ........... *G16H 50/70* (2018.01); *H04L 9/3213* (2013.01); *H04L 9/50* (2022.05); *H04L 2209/88* (2013.01)

(58) Field of Classification Search
CPC ........ G16H 50/70; G16H 10/60; G16H 50/20; H04L 9/3213; H04L 9/50; H04L 2209/88; G06F 16/9535; G06F 16/275; G16B 50/20
See application file for complete search history.

(56) References Cited

U.S. PATENT DOCUMENTS

| | | | |
|---|---|---|---|
| 7,984,014 B2 | 7/2011 | Song et al. | |
| 9,165,109 B2 | 10/2015 | Chaisson | |
| 11,443,855 B2* | 9/2022 | Pavlatos | ............... H04L 9/3213 |
| 2002/0052761 A1* | 5/2002 | Fey | ........................ G06Q 10/10 |
| | | | 705/2 |
| 2013/0226621 A1 | 8/2013 | Van Der Zaag et al. | |
| 2015/0248525 A1 | 9/2015 | Ury et al. | |

(Continued)

OTHER PUBLICATIONS

National Academies of Sciences, Engineering, and Medicine, "Understanding Disparities in Access to Genomic Medicine: Proceedings of a Workshop," The National Academic Press, 2018, 127 pages.

(Continued)

*Primary Examiner* — Ka Shan Choy
(74) *Attorney, Agent, or Firm* — Fish & Richardson P.C.

(57) ABSTRACT

A system includes a first database to store assessments of genomic tests; a second database to store evaluations of the assessments; one or more processors, and storage media storing instructions that, when executed, cause the processors to perform operations including: receiving information about a genomic test; sending, to a group of clinical experts, notification about availability of the information; receiving, from one or more clinical experts, assessments of the information; storing the assessments in the first database; processing the assessments by applying one or more functions on an aggregate of the assessments, including comparing an output of the functions to a threshold; determining a result indicating a status of the genomic test; and storing one or more of the result or the information about the genomic test in the second database. Consumers are enabled to access one or more of the result or the information about the genomic test.

24 Claims, 6 Drawing Sheets

(56) References Cited

U.S. PATENT DOCUMENTS

2015/0332283 A1* 11/2015 Witchey .................. G06F 21/00
                                                                  705/3
2016/0371446 A1* 12/2016 Otin ....................... G16H 40/63
2019/0305956 A1* 10/2019 Irani, III ............... G06Q 20/389
2020/0227160 A1*  7/2020 Youngblood .......... G16H 40/20
2020/0327996 A1* 10/2020 Barkol ................... G16H 80/00

OTHER PUBLICATIONS

PCT International Preliminary Report on Patentability in International Appln. No. PCT/US2020/041976, dated Jan. 18, 2022, 10 pages.
PCT International Search Report and Written Opinion in International Appln. No. PCT/US2020/041976, dated Sep. 30, 2020, 12 pages.

* cited by examiner

```
400
```

┌─────────────────────────────────────────────────────────────────────────┐
│ Receive, from a particular consumer, particular patient data corresponding to administration of a │
│ particular genomic test on a particular patient                                               402 │
└─────────────────────────────────────────────────────────────────────────┘
                                         ↓
┌─────────────────────────────────────────────────────────────────────────┐
│ Store, in a third database, the particular patient data along with one or more other patient data │
│ corresponding to other administrations of the particular genomic test on other patients      404 │
└─────────────────────────────────────────────────────────────────────────┘
                                         ↓
┌─────────────────────────────────────────────────────────────────────────┐
│ Enable a third party to access patient data for the particular genomic test from the third database │
│ upon authorization by an administrator                                                        406 │
└─────────────────────────────────────────────────────────────────────────┘
                                         ↓
┌─────────────────────────────────────────────────────────────────────────┐
│ Analyze aggregate patient data, including determining, using the aggregate patient data, one or │
│ more clinical patterns corresponding to the particular genomic test                          408 │
└─────────────────────────────────────────────────────────────────────────┘
                                         ↓
┌─────────────────────────────────────────────────────────────────────────┐
│ Store the analysis data in a fourth database                                                  410 │
└─────────────────────────────────────────────────────────────────────────┘
                                         ↓
┌─────────────────────────────────────────────────────────────────────────┐
│ Enable a third party to access patient data for the particular genomic test from the fourth │
│ database upon authorization by an administrator                                               412 │
└─────────────────────────────────────────────────────────────────────────┘
                                         ↓
┌─────────────────────────────────────────────────────────────────────────┐
│ Implement a compensation procedure with one or more of the particular consumer or the third │
│ party                                                                                         414 │
└─────────────────────────────────────────────────────────────────────────┘

FIG. 4

DISTRIBUTED MEDICAL TESTING FRAMEWORK

CROSS-REFERENCE TO RELATED APPLICATIONS

This application is a continuation-in-part of International Application No. PCT/US2020/041976, filed Jul. 14, 2020, and claims the benefit of priority of U.S. Provisional Application No. 62/875,590, filed Jul. 18, 2019, the contents of which are incorporated here by reference in their entirety.

TECHNICAL FIELD

The following disclosure relates generally to a distributed medical testing framework, and in particular, to systems, devices and methods related to a distributed framework for providing information about genomic tests for public dissemination.

BACKGROUND

Consumer genomic testing (which includes genetic testing) provides a means of allowing consumers to access information on their genetics with limited involvement of a physician. There is, however, a dearth of skilled medical genetics practitioners, with many populations that are underserved. For example, there is an uneven geographic distribution of such practitioners, with clusters of practitioners in urban areas centered around academic medical centers, but with practitioners often unavailable in rural areas. In general, medical providers who focus on other types of medical fields may not have the genomics expertise that is needed to interpret the consumer genomic tests and provide appropriate care for their patients. In addition, these tests (which may not be stringently regulated by the FDA) are becoming widely available directly to the general public, often without provision of unbiased information or a coherent system to collect consumer post-market data.

SUMMARY

The present disclosure describes systems, devices and methods related to a distributed medical testing framework (also referred to as the "framework") that provides access on a global scale to information about medical tests and associated clinical interpretations. In some implementations, the framework includes a system with network-connected servers, databases and computers, which work together to provide access to clinical information about state-of-the-art consumer genomic tests, such as genomic diagnostic and screening tests, to consumers (both individuals and medical providers) who are widely distributed geographically. In such implementations, the framework facilitates consensus building among clinical subject matter experts about clinical claims of consumer genomic tests, who provide individual assessments of the clinical claims for genomic tests that are available using the framework. The framework applies one or more computational tools, to form a consensus of the current clinical claims of consumer genomic tests based on the individual assessments from the clinical experts. The framework disseminates the consensus results to consumers distributed globally, through network portals that are accessible to individuals and medical providers. In some implementations, the medical providers are generalists who do not have genomics expertise or knowledge. However, in some other implementations, the medical providers are genetics providers with genomics expertise or knowledge.

In some implementations, the computational tools used in the framework include blockchain-based consensus building mechanisms. For example, in such cases, the tools are used to compare aggregates of assessments from the clinical experts about a consumer genomic test to pre-set thresholds or quorum size. Depending on the results of the comparison, the expert assessments are submitted as transactions in a blockchain maintained by the framework, either validating or refuting the clinical claim provided for the particular consumer genomic test.

In some implementations, the consensus results disseminated through the framework are accompanied by additional medical information about the corresponding genomic tests. For example, the medical information includes scientific background knowledge about the corresponding genomic test, which is provided to familiarize the consumer with the test. In some implementations, the additional medical information is included as fields in transaction blocks of the blockchain.

In some implementations, the framework provides a mechanism for the consumers to provide feedback on the genomic tests, for example, by uploading to the network portal provided by the framework, clinical outcomes of the particular genomic tests labeled with a unique device identifier (UDI) that is mandated by the FDA for each individual test. In some implementations, the consumers are enabled to upload patient data along with the information on the clinical outcomes of the genomic tests. In some implementations, the clinical outcomes are submitted as transactions in a blockchain maintained by the framework. In some implementations, the blockchain hosting the expert assessment transactions is same as the blockchain hosting the clinical outcomes transactions. However, in other implementations, these are independent, or quasi-independent blockchains.

In some implementations, the framework includes a mechanism for financial transactions corresponding to information regarding the genomic tests. For example, in some cases, the clinical experts are compensated for their assessments, while the consumers are charged for access to the results. In some cases, the medical providers or individuals, or both, are compensated for sharing the clinical outcomes. In some implementations, the financial transactions are performed using cryptocurrencies. In such cases, the financial transactions are recorded as blocks in a blockchain, which can be same as the one of the blockchains hosting the expert assessment transactions or the clinical outcomes transactions, or different.

In a general aspect, a system includes a first database that is configured to store assessments of genomic tests and is accessible by clinical experts, wherein a clinical expert is enabled to access the first database upon authorization by an administrator. The system includes a second database that is configured to store evaluations of the assessments, wherein the second database is accessible upon authorization by the administrator. The system also includes one or more processors, and storage media having stored thereon instructions that, when executed by the one or more processors, cause the one or more processors to perform operations that include: receiving an input including information about a particular genomic test (such as input provided by an industry participant or by a source (e.g., an algorithm) that determined the input based on consumer feedback or test result data); in response to receiving the information, sending, to a group of the clinical experts, a notification about availability of the information; receiving, from one or more of the group of the clinical experts, particular assessments of the information; storing the particular assessments in the first database; processing the particular assessments by applying one or more functions operating on an aggregate of the particular assessments, the processing including comparing an output of the one or more functions to a preselected threshold; in response to the processing, determining a result indicating a status of the particular genomic test; and storing one or more of the result or the information about the particular genomic test in the second database. The second database may be accessible to consumers upon authorization by the administrator. In some implementations, the consumers are enabled, with authorization, access one or more of the result or the information about the particular genomic test for patient diagnostic or screening tests.

Particular implementations of the system may include one or more of the following features. The information about the particular genomic test may be provided by an industry participant. The industry participant may include a genomic testing company that created the particular genomic test. The information about the particular genomic test may include clinical claims about the particular genomic test.

The information about the particular genomic test may be provided by an industry participant or based on consumer feedback, such as output of an algorithm discerning new information about the particular genomic test by analyzing consumer feedback data.

The information about the particular genomic test may include one or more of test make, test model, test model version, a set of possible results of the particular genomic test and corresponding claim interpretations, clinical factors corresponding to anomalous results, or consumer outcome data (such as a result of data analysis of consumer outcome data). The claim interpretations may include one of: a positive interpretation of the set of possible results of the particular genomic test, a negative interpretation of the set of possible results of the particular genomic test, or an indeterminate interpretation of the set of possible results of the particular genomic test. The claim interpretations may include interpretations based on data analysis of consumer feedback.

Receiving the particular assessments (such as clinical assessments) of the information from one or more of the group of the clinical experts may include receiving, from at least one clinical expert of the group of the clinical experts, a transaction in a blockchain, the transaction including an identifier (such as a product identifier and/or a device identifier) of the particular genomic test and authenticated using a cryptographic identifier corresponding to the at least one clinical expert. Storing the particular assessments in the first database may include storing the transaction as a block of the blockchain in the first database.

Processing the particular assessments by applying one or more functions on the aggregate of the particular assessments may include applying a consensus testing mechanism on an aggregate of transactions that include the identifier of the particular genomic test. The transactions may include respective cryptographic identifiers corresponding to the clinical experts providing the transactions. Comparing the output of the one or more functions to the preselected threshold may include determining whether a number of assessments of the particular genomic test meet a quorum size. The consensus testing mechanism may be applied to an aggregate of the transactions that are weighted using one or more weighting values, wherein a weighting value may be based on one or more of: a recency of a corresponding assessment, expertise of a corresponding clinical expert, a sample size, a negative assessment of the particular genomic test, or a positive assessment of the particular genomic test.

A particular assessment of the information may include an acceptance or rejection assessment of the particular genomic test based on one or more of expert knowledge of the clinical expert, experience of the clinical expert, clinical guidelines adopted by the clinical expert, or a statistical analysis of internal clinical records.

A particular assessment of the information may include a statistical summary of clinical actions taken for specific results of the particular genomic test.

Storing one or more of the result or the information about the particular genomic test in the second database may include adding the result as a transaction in a blockchain stored in the second database, the transaction including an identifier of the particular genomic test and authenticated using a cryptographic identifier corresponding to the administrator. The transaction may include one or more identifiers of experts who provided assessments leading to the result. The transaction may further include one or more of recommended clinical actions for the particular genomic test provided by one or more of the group of the clinical experts, a summary of clinical data corresponding to the particular genomic test, or educational information to interpret the particular genomic test. The system may further include a server coupled to the second database and configured to provide the result or the information about the particular genomic test to connected client devices. Providing the result or the information about the particular genomic test may include enabling a client device of a consumer to establish a network connection to the server using a blockchain-based browser; and presenting one or more of the result or the information about the particular genomic test on a user interface blockchain-based browser, the user interface shown on the client device.

Receiving the input including information about the particular genomic test may further include storing the information in the second database a third database, wherein the industry participant or a qualified administrator may be enabled to access the third database upon authorization by the administrator, wherein the operations may further include enabling the group of the clinical experts to access the information. The third database may be configured to store the information about the particular genomic test as a transaction in a blockchain, the transaction authenticated using a cryptographic identifier corresponding to the industry participant or a cryptographic identifier corresponding to a source that analyzed consumer feedback data to determine the information.

The system may further include a third database storing contextual educational information about the particular genomic test, wherein the third database may be accessible by the administrator, and wherein the operations may further include storing, with one or more of the result or the information about the particular genomic test stored in the second database, a link to the contextual educational information. The contextual educational information may include one or more of a technical description of a test platform for the particular genomic test, a functional biological basis for the particular genomic test, a technical or biological factor causing an indeterminate result, or a general limitation regarding applicability of the particular genomic test to certain patients. The contextual educational information about the particular genomic test may be stored in the third database as a transaction in a blockchain of the third database, the transaction including an identifier of the particular genomic test and authenticated using a cryptographic identifier corresponding to the administrator.

The system may further include a third database that is configured to store patient data corresponding to particular medical test instances and a fourth database that is configured to store analytical information corresponding to the patient data, wherein the consumer may be enabled to access the third database upon authorization by the administrator. The operations may further include: receiving, in the third database from a particular consumer, particular patient data corresponding to administration of the particular genomic test on a particular individual; obtaining aggregate consumer data for the particular genomic test by combining the particular patient data with one or more other consumer data corresponding to other administrations of the particular genomic test on other consumers analyzing the aggregate consumer data, including determining, using the aggregate consumer data, one or more clinical patterns corresponding to the particular genomic test; storing the one or more clinical patterns in the fourth database; and publishing information about availability of the one or more clinical patterns in the fourth database, wherein this information may be transferred to the claims database and or wherein a third party may be enabled to access the one or more clinical patterns from the fourth database upon authorization by the administrator. The particular patient data may include a device identifier labeling a specific test used to obtain the particular patient data.

The particular patient data may include one or more of clinical validity information of the administration of the particular genomic test on the particular patient, clinical utility information of the administration of the particular genomic test on the particular patient, or analytical validity information corresponding to the administration of the particular genomic test on the particular patient. The one or more clinical patterns may include one or more of sensitivity or specificity of the particular genomic test, positive predictive value of the particular genomic test, negative predictive value of the particular genomic test, or accuracy of the particular genomic test. The one or more clinical patterns may include personal characteristics of patients, disease states of patients, genetic variation among patients, or imaging test results.

Analyzing the aggregate patient data may include processing the aggregate patient data using data mining tools. Analyzing the aggregate patient data may include processing the aggregate patient data using artificial intelligence-based analytical tools.

The one or more clinical patterns may be stored in the fourth database as a transaction in a blockchain, the transaction including an identifier of the particular genomic test and authenticated using a cryptographic identifier corresponding to the administrator.

Enabling the third party to access the one or more clinical patterns from the fourth database upon authorization by the administrator may include: receiving, from the third party, a predetermined amount of cryptocurrency tokens; and in response to receiving the predetermined amount of cryptocurrency tokens, enabling, by the administrator, the third party to access the one or more clinical patterns from the fourth database. The cryptocurrency tokens may be managed as blocks in the blockchain.

The genomic tests may include consumer diagnostic genomic tests. Receiving the input including information about the particular genomic test may include receiving the input from the administrator. Receiving particular assessments of the information from one or more of the group of the clinical experts may include receiving, from a plurality of the group of the clinical experts, particular assessments of the information. Receiving, from one or more of the group of the clinical experts, particular assessments of the information may further include providing, to a clinical expert of the group of the clinical experts, a predetermined amount of cryptocurrency tokens as a payment for a particular assessment received from the clinical expert.

The system may further include providing, to the industry participant, a predetermined amount of cryptocurrency tokens as a payment for the information about the particular genomic test received from the industry participant.

Enabling the consumers to access one or more of the result or the information about the particular genomic test for patient diagnostic or screening tests may further include receiving, from a consumer, a predetermined amount of cryptocurrency tokens for enabling the consumer to access one or more of the result or the information about the particular genomic test.

The operations may include receiving, from a consumer, a predetermined amount of cryptocurrency tokens; and in response to receiving the predetermined amount of cryptocurrency tokens, providing the consumer access to at least one of the result or the information about the particular genomic test in the second database.

The system may include a blockchain database. The operations may include receiving, from a consumer, medical data including an outcome of the particular genomic test administered to a patient, and patient information characterizing the patient; and, in response to receiving the medical data, providing, to the consumer, a predetermined amount of cryptocurrency, and storing the medical data in the blockchain database.

The system may include a third database that is configured to store medical data including a result of the particular genomic test administered to a patient, and patient information characterizing the patient. The system may include a blockchain database that is configured to store a non-fungible token corresponding to the medical data, wherein the non-fungible token includes an identifier of the medical data.

The blockchain database may include a smart contract that, when invoked, is configured to determine that an invoker of the smart contract is an owner of the non-fungible token, and, in response to determining that the invoker is the owner of the non-fungible token, provide the medical data to the invoker of the smart contract.

The blockchain database may include a smart contract that, when invoked, is configured to receive the medical data from an invoker of the smart contract, store the medical data in the third database, generate the non-fungible token, and provide, to the invoker of the smart contract, a predetermined amount of cryptocurrency.

The blockchain database may include a smart contract managed by a decentralized autonomous organization. Membership in the decentralized autonomous organization may correspond to ownership of tokens of the blockchain database, and the smart contract may be invocable to alter parameters of one or more other smart contracts of the blockchain database.

The operations may include receiving, from a third party, a predetermined amount of cryptocurrency tokens stored in the blockchain, and, in response to receiving the predetermined amount of cryptocurrency tokens, enabling the third party to access the one or more clinical patterns from the fourth database.

Implementations of the above techniques include methods, apparatus, systems and computer readable media. One such method includes the above-described actions. One or more non-transitory computer-readable media store instructions executable by one or more processors. The instructions, when executed by the one or more processors, are configured to cause the one or more processors to perform the above-described actions. Another such system includes one or more processors and one or more storage media storing instructions that, when executed by the one or more processors, are configured to cause the one or more processors to perform the above-described actions.

The medical testing framework enables access to knowledge and interpretations of state-of-the-art consumer genomic tests to consumer i.e. individuals or medical providers who may lack specialized knowledge about these tests or may not be trained in these tests, or both. Unbiased evaluations of clinical claims of the consumer genomic tests are distributed without modifications or alternations based on a consensus built by independent clinical experts, with no third-party adjudication across the healthcare system. In doing so, the framework addresses the bottleneck created by the dearth of genetic counselors in underserved areas. The framework restricts access to authorized clinical experts or medical providers, which helps to avoid compromising confidential patient information, compared to unrestricted transmissions over the internet. The use of blockchain-based transactions for the assessments of the clinical claims ensures that the assessments are securely authenticated and can be traced to particular clinical experts. At the same time, anonymity of the clinical experts is guaranteed, with the framework acting as the intermediary between the clinical experts and the consumers.

The medical information provided with the results allow consumers to familiarize themselves with the background information needed to interpret consumer genomic tests, which enhances the ability for consumers to make informed medical decisions. By allowing medical providers or their patients, or both, to send feedback for clinical outcomes of particular tests, the framework enables evidence-based outcome analysis, which is useful to determine clinical validity or clinical utility of the genomic tests. The accompanying structure for financial transactions to compensate the clinical experts, the medical providers or the individuals, as applicable, facilitates a decentralized, incentive-based mechanism, for knowledge sharing about genomic tests.

The details of one or more disclosed implementations are set forth in the accompanying drawings and the description below. Other features, aspects, and advantages will become apparent from the description, the drawings and the claims.

BRIEF DESCRIPTION OF THE DRAWINGS

FIG. 4 illustrates an example of a process to manage clinical outcomes for a genomic test using a distributed medical testing framework.

DETAILED DESCRIPTION

Figure 1:
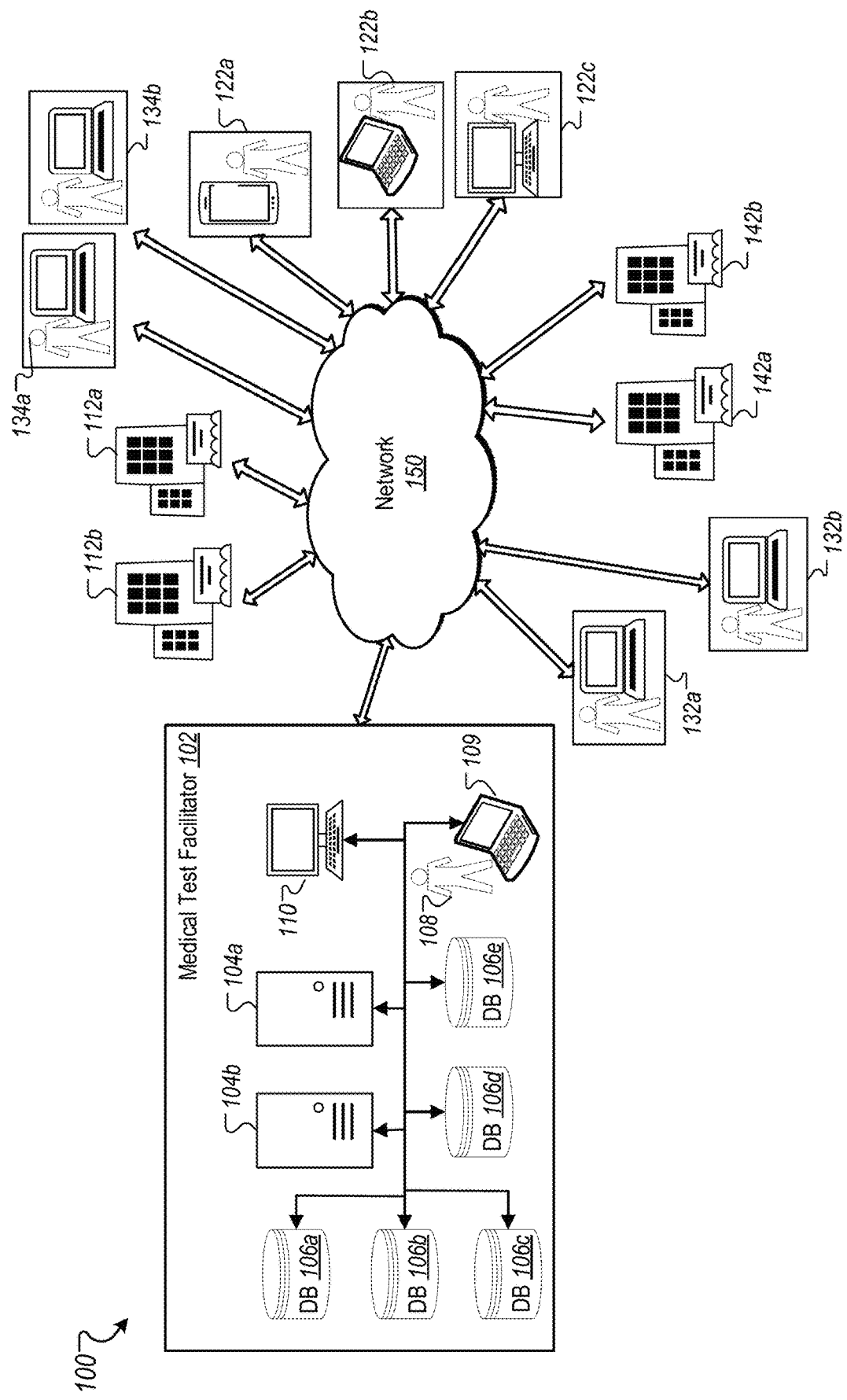
FIG. 1 illustrates an example of a system that provides a distributed medical testing framework.

Consumer genomic testing allows consumers to access information on their genetics with minimal or no involvement of a physician. Although consumer genomic tests are popular with consumers, there is a dearth of skilled medical genetics practitioners. Medical genetics is a small medical subspecialty and many populations, for example, rural areas or developing countries, are not well served by medical geneticists or genetic counselors. Where genetic providers are available, there is an uneven geographic distribution of the providers, with clusters of genetic providers in urban areas around academic medical centers. Medical providers in other areas often do not have the genomics expertise that is needed to interpret the genomic tests and provide appropriate care for their patients. The accuracy and uniformity of interpreting consumer genomic tests can thus vary greatly depending on the location. In some instances, the interpretations of these tests are left to the consumers themselves. If misinterpreted, these tests can confuse the patient and put him or her at risk of making health decisions on inaccurate or incomplete information.

The lack of a comprehensive reimbursement or compensation system is also an issue, since consumer tests are often purchased by consumers through out-of-pocket payments outside of a special medical setting that provide genetic counseling. Consumers (for example, patients or medical providers, or both) frequently rely on developers of the genomic tests for the interpretation of test results. Genetic counselors working with the test developers can be subject to conflicts of interest.

Some genomic tests, for example, non-invasive pre-natal tests (NIPT) and nutrigenetics, which are not under the normal rigor of governmental regulations, can be accessible to consumers with limited regulatory supervision. Medical providers rely on continuing education courses to learn the relevant scientific background that is needed to interpret such genomic tests. However, there is a considerable lag between availability of these tests in the market and the time medical providers need to acquire the relevant expertise. There is thus an unmet need not only to find a viable mechanism to disseminate information on the state-of-the-art interpretations pertaining to the analytical and clinical validity of the genomic tests, but also a method to familiarize the medical practitioners with the reverent background scientific knowledge. Current attempts to provide clinical claims or interpretations of genomic tests to consumers include telephone delivery of genetic counseling and incorporating narrative-based videos and community health navigators into genetic service delivery models, and incorporating genetic and genomic information in electronic health records to be used for clinical decision making and rapid learning This specification describes a distributed framework for medical tests that enables consumers (for example, medical providers or patients, or both) to access authenticated evaluations of clinical claims of consumer genomic tests based on assessments provided by subject matter experts. The consumers can be located in any geographic region, and can access the test interpretations in a secure manner through wide area network connections to servers and databases hosting the test information. In some implementations, the framework provides educational information accompanying the clinical claims, enabling consumers globally to familiarize themselves with the background information needed to interpret the consumer genomic tests, enhancing their ability to provide better guidance to patients. In some implementations, the framework also includes a feedback mechanism that empowers medical providers or patients, or both, to post feedback about their experiences corresponding to particular genomic tests, which enable evidence-based outcome analysis that is useful to decipher the clinical validity as well as clinical utility of the genomic tests. This new information can be accessed by clinical experts and distributed back to consumers via the framework.

In some implementations, the information is managed by the framework as transactions in blockchains stored in databases. The use of blockchains allows decentralized authentication and accounting of evaluations of the clinical claims, educational information or provider feedback, and prevents alterations to any submitted transaction. The blockchains also facilitate tight coupling of financial transactions, for example, to compensate clinical experts providing assessments or consumers for posting feedback, or to charge consumers for accessing test interpretations. Some implementations of the blockchains facilitate data transfer and management in the form of on-blockchain non-fungible tokens (NFTs) that regulate ownership of, and/or access to, medical data such as genomic test outcomes and related clinical data. In some implementations, the NFTs can be managed according to consensus decisions in a decentralized autonomous organization (DAO) to provide improved transparency for medical data access.

FIG. 1 illustrates an example of a system 100 that provides a distributed medical testing framework. The system 100 includes a medical test facilitator 102, one or more industry participants 112a and 112b, one or more clinical experts 122a, 122b and 122c (collectively, clinical experts 122a-122c), one or more consumers (including medical providers 132a-132b and/or individuals 134a-134b), and one or more organizations 142a and 142b. The system 100 also includes a communications network 150 that connects various other entities to one another through network connections.

The medical test facilitator 102 provides the distributed medical testing framework. In some implementations, the medical test facilitator 102 is an organization, for example, a corporation, which provides hardware and software systems and services for storing and managing information about consumer genomic tests and corresponding clinical claims, expert assessments of these tests, test feedbacks, and financial transactions. As shown, the medical test facilitator 102 includes one or more computer servers 104a and 104b, one or more databases (DB) 106a, 106b, 106c, 106d and 106e (collectively, databases 106a-106e), and one or more personal computers, such as a laptop computer 109 and a desktop terminal 110. The systems and services of the medical test facilitator 102 are managed by one or more human operators, represented by administrator 108.

In some implementations, the various hardware of the medical test facilitator 102—the computer servers 104a and 104b, databases 106a-106e, laptop computer 109 and desktop terminal 110—are in a common location, for example, in an office building, and connected to one another through a local area network (LAN). In other implementations, the various hardware of the medical test facilitator 102 are geographically distributed, for example, across multiple office locations, and connected to one another through a wide area network (WAN), for example, through the network 150.

The industry participants 112a and 112b develop medical tests for consumers. In some implementations, the industry participants include genomic testing companies that develop genomic tests. In some implementations, the genomic tests include screening tests, for example, genomic tests that look at a probability of whether a particular genetic condition is present, without giving a definitive 'yes' or 'no' answer. A screening test can be performed on asymptomatic members of a population to assess the likelihood of one or more members of the population having a particular disease. There are no or limited health complications with screening tests. In some implementations, the genomic tests include diagnostic tests, for example, tests that determine whether a particular genetic condition is present with substantial (for example, 90% or 100%) accuracy. A diagnostic test can be given to symptomatic people to help determine whether someone has a particular disease at the time the test is performed. In some implementations, the genomic tests include prognostic tests, which can be used to predict the likelihood of an individual developing a particular disease or experiencing a particular medical event, or both. In some cases, the genomic tests include unregulated tests, for example, genomic tests that are not overseen by regulatory agencies. In such cases, the industry participants 112a and 112b develop consumer genomic tests, which provide patients access to their genetic information, often without involving a medical provider with specialized knowledge or a health insurance company in the process. Different industry participants can be in different locations, for example, in different countries, or different regions of a country.

The clinical experts 122a, 122b and 122c are subject matter experts in various genetic traits. As shown, the clinical experts interact with other entities in the system 100 using computing devices, such as desktop computers, laptop computers, tablet computers or smartphones. Different clinical experts can be experts in different genetic traits, and a clinical expert can be an expert in more than one genetic trait. The clinical experts can be scientists, researchers, academicians, or physicians. The clinical experts can work in various fields, for example, industry, research institutes, or universities. The clinical experts can be in different locations, for example, in different countries, or different regions of a country.

The medical providers 132a and 132b can be practitioners who provide medical services to patients, such as, for example, physicians, nurses, medical counselors, and/or health advocates. The individuals 134a-134b can be consumers, patients, and/or other people who seek medical services. The medical services can include counseling related to various genetic traits and advice on clinical claims of the genomic tests corresponding to the genetic traits. In some implementations, the genomic tests include non-invasive pre-natal tests (NIPT) or nutrigenetics, or both. The medical providers 132a, 132b and/or individuals 134a, 134b interact with other entities in the system 100 using computing devices, such as desktop computers, laptop computers, tablet computers or smartphones.

In some implementations, the medical providers 132a and 132b are generalists without specialized knowledge of genomic tests. In some other implementations, however, one or more of the medical providers 132a and 132b are skilled medical genetics practitioners. Different medical providers can be in different locations, for example, in different countries, or different regions of a country. In some implementations, one or more of the medical providers 132a and 132b practice with underserved populations, for example, in rural areas or in developing countries. However, in some other implementations, one or more of the medical providers 132a and 132b practice in well-served urban areas or developed countries.

The organizations 142a and 142b include organizational entities of various types that are interested in knowing about clinical outcomes of genomic tests, for example, whether the real-world results conform to the initial clinical claims of the tests, or not. The organizations 142a and 142b include, for example, academic centers of excellence such as universities or research institutions, regulatory agencies, professional registries, international health agencies, among others. Different organizations can be in different locations, for example, in different countries, or different regions of a country.

The network 150 is a wide area network (WANs) that connects the different components of the system 100 over network connections. In some implementations, the network 150 is a combination of various public and private networks, for example, the Internet. In some implementations, the network 150 is an enterprise network, for example, a virtual private network over the Internet.

In operation, the distributed medical testing framework is realized using one or more of the servers, databases and computers of the medical test facilitator 102. For example, in some implementations, the distributed medical testing framework includes a network-connected portal, for example, a website, that is hosted by the server 104a or 104b, or a combination of the two. Without loss of generality, in the following description, the server 104a is referred to as performing various operations for the framework. It should be understood that the operations are also applicable to other components of the medical test facilitator, for example, server 104b, laptop computer 109 or desktop computer 110.

One or more stakeholders, for example, industry participants 112a or 112b, clinical experts 122a-122c, an individual 134a or 134b, or medical providers 132a or 132b, can register with the distributed medical testing framework through an online portal, for example, a webpage interface, provided by the website. In some implementations, the administrator 108 manages the registration of the various stakeholders. For example, the administrator 108 accepts or denies registration requests. For accepted requests, the administrator 108 authorizes access to the website, for example, by providing login credentials such as username and password, to the registrants.

In some implementations, as part of the registration, a stakeholder exchanges cryptographic security information with the hosting server. For example, when clinical expert 122a registers using her corresponding computing device, the computing device advertises a public cryptographic key of clinical expert 122a to the server 104a. The computing device uses the corresponding private key to authenticate transactions performed in the distributed medical testing framework, for example, to perform hash authentication for blockchain transactions initiated by the clinical expert 122a. In some implementations, the server 104a shares copies of the blockchains used in the distributed medical testing framework with the computing device of the clinical expert 122a. In some implementations, the server 104a also distributes the identity of the clinical expert 122a or the corresponding public key, or both, to other stakeholders.

When an authorized industry participant, for example, industry participant 112a or 112b, wants to submit a new genomic test information to the distributed medical testing framework, the industry participant logs in to the website through the online portal using its login credentials and uploads the genomic test to the server 104a. The industry participant's clinical claims, for example, interpretation of the test, are uploaded along with the test. In some cases, a representative of the medical test facilitator 102, e.g., administrator 108 or a genetic expert employee, receives the information about the new genomic test and uploads the information to the server 104a.

The server 104a stores the test and the corresponding clinical claim in storage memory coupled to the server. In some implementations, the genomic test and the corresponding clinical claim is stored in a claims database maintained by the medical test facilitator 102. For example, in such cases, the medical test facilitator 102 maintains the claims database in one of the databases 106a-106e, such as database 106a. In some implementations, the medical test facilitator 102 financially compensates the industry participant for submission of the new genomic test. In some implementations, cryptocurrency tokens are used for the financial compensation. In some implementations, no compensation mechanism is present. More details about the claims database are described with respect to the system 200 of FIG. 2.

In some implementations, data in the server 104a includes new information about an existing test. For example, consumer feedback or consumer results obtained by the medical test facilitator 102 can indicate that an existing test tends to provide incorrect results. The consumer feedback or results can be stored (e.g., in the claims DB 206a) and analyzed by the medical test facilitator 102 using one or more analysis methods (e.g., machine learning methods and/or algorithms), such as analysis methods performed by the server 104a. When the server 104a determines that a clinical claim about a test should be re-analyzed based on new information (e.g., based on consumer feedback about the test or consumer results of the test), the server 104a can provide the new information to clinical experts for validation.

In some implementations, following upload of a new genomic test, and/or for validation of an existing test (e.g., a test stored in a database 106a-106e), the server 104a sends a notification to one or more of the clinical experts 122a-122c who are registered with the distributed medical testing framework about availability of the new test. In some implementations, the notification is sent only to those clinical experts who are subject matter experts in the field corresponding to the new test. In some other implementations, the notification is sent to all registered clinical experts. The notification, which is received at the computing devices of the clinical experts, can include a link to access the new test, or a brief description of the test, or both.

One or more of the clinical experts 122a-122c (e.g., having received the notification) can access the new genomic test. In some implementations, the clinical experts log in through the online portal using respective login credentials and access the genomic test from the server memory or claims database. In some other implementations, the clinical experts access the genomic test using the link sent with the notification.

After reviewing the genomic test and corresponding clinical claim from the test developer, the clinical experts provide their assessments of the clinical claim. In some implementations, a clinical expert uploads her or his assessment to the server 104a through the online portal. The server 104a stores the assessment in memory coupled to the server. In some implementations, the expert assessments are stored in an expert database maintained by the medical test facilitator 102. For example, in such cases, the medical test facilitator 102 maintains the expert database in one of the databases 106a-106e, such as database 106b.

In some implementations, the expert database maintains a blockchain and a clinical expert submits her assessment as a transaction in the blockchain. In some implementations, the expert database is accessible to only authorized clinical experts and officers of the distributed medical testing framework, such as the administrator 108. In some other implementations, the expert database is also accessible to other stakeholders, such as individuals (for example, individuals 134a and/or 134b), medical providers (for example, medical providers 132a or 132b), organizations (for example, organizations 142a or 142b), or industry participants (for example, industry participants 112a or 112b), or any suitable combination of these stakeholders.

In some implementations, the medical test facilitator 102 financially compensates the clinical experts for submission of their assessments. In some implementations, cryptocurrency tokens (e.g., Bitcoin, Ethereum, Litecoin, Dogecoin, or another suitable cryptocurrency) are used for the financial compensation. More details about the expert assessments, the expert database and corresponding blockchain are described with respect to the system 200 of FIG. 2.

The assessment of a genomic test by an expert indicates either acceptance of the clinical claim corresponding to the genomic test, rejection of the clinical claim, or an indeterminate result. In some implementations, more than one expert evaluates a genomic test. In such cases, when an expert submits her assessment, the server 104a executes instructions to incorporate the expert assessment with assessments of the same genomic test by other experts, to arrive at an overall determination or result about the clinical claim of the genomic test. In some other implementations, a single expert evaluates a genomic test. In such cases, when an expert submits her assessment, the server 104a arrives at a result about the clinical claim of the genomic test based on the sole assessment. The operations performed by the server to arrive at the result, including use of algorithmic tools and mechanisms, are described with respect to the system 200 of FIG. 2.

The server 104a publishes the determination about the clinical claim of the genomic test in a consensus database. In some implementations, the medical test facilitator 102 maintains the consensus database in one of the databases 106a-106e, such as database 106c. The consensus database includes information about all genomic tests that have been reviewed and evaluated by clinical experts, along with corresponding determinations about the genomic tests based on the expert assessments. In some implementations, the consensus database is accessible by authorized consumers (for example, medical providers 132a or 132b), and/or individuals (for example, individuals 134a or 134b), organizations (for example, organizations 142a or 142b), industry participants (for example, industry participants 112a or 112b), or clinical experts (for example, clinical experts 122a-122c), or any suitable combination of these stakeholders. In some other implementations, the consensus database is accessible to any member of the public. More details about the consensus database are described with respect to the system 200 of FIG. 2.

In some implementations, the administrator 108 (or another officer of the medical test facilitator 102) uploads, to the server 104a, educational material for particular genomic tests that are available in the consensus database. In some implementations, the server 104a stores the educational material in an educational database maintained by the medical test facilitator 102, with the information linked to a corresponding genomic test in the consensus database. For example, in such cases, the medical test facilitator 102 maintains the educational database in one of the databases 106a-106e, for example, database 106d. In some implementations, the educational database maintains a blockchain and the educational information for a specific genomic test is stored as a transaction in the blockchain. In some implementations, the server 104a stores the educational material in the consensus database, for example, as an entry for the corresponding genomic test. More details about the educational information and the educational database are described with respect to the system 200 of FIG. 2.

In some implementations, consumers, for example, medical providers 132a, 132b and/or individuals 134a, 134b, can access the consensus database by logging in through the online portal using their login credentials. A consumer can look up a genomic test corresponding to a target genetic trait that is of significance to a patient and download the clinical claim of the test along with the result of evaluation of the assessments from the clinical experts. In some implementations, the consumer can also download the educational information corresponding to the genomic test of interest that is available in the distributed medical testing framework, for example, either as an entry in the consensus database or in the educational database. In some implementations, the consumer makes a payment to the medical test facilitator 102 for access to the data in the consensus database. In some implementations, the payment is made in the form of cryptocurrency tokens.

In some implementations, consumers, for example, medical providers 132a, 132b and/or individuals 134a, 134b, provide outcome information regarding the clinical validity and clinical utility of individual genomic tests to the distributed medical testing framework. The outcome information can include test results. For example, an individual or medical provider may access a particular genomic test and corresponding clinical claim from the consensus database, and the test can be administered. At a later time, after outcome information is available for application of the test on a patient (e.g., the individual), the individual or medical provider (with the consent of the patient) may upload the outcome information to the server 104a. The outcome information can be linked to an NFT, as described in further detail with respect to FIG. 6. In this context, clinical validity refers at least to how well a genetic variant being analyzed is related to the presence, absence, or risk of a specific disease. Clinical utility refers to whether a genomic test can provide information about diagnosis, treatment, management, or prevention of a disease that will be helpful to a consumer. In some implementations, the medical test facilitator 102 financially compensates the consumers for submission of outcome information. In some implementations, cryptocurrency tokens are used for the financial compensation.

In some implementations, the server 104a stores the outcome information in a clinical outcome database maintained by the medical test facilitator 102. For example, in such cases, the medical test facilitator 102 maintains the clinical outcome database in one of the databases 106a-106e, for example, database 106e. In some implementations, the clinical outcome database maintains a blockchain and the outcome information for a particular patient is stored as a transaction in the blockchain. In some implementations, interested stakeholders, for example, one or more of organizations 142a or 142b, can access the outcome information for a particular genomic test, uploaded by various medical providers or patients, from the outcome database. In some implementations, the medical test facilitator 102 makes the data mining output information available to the interested stakeholders, for example, organization 142a or 142b, in exchange for financial compensation. In some instances this information is sent into the claims database 106a to be accessed by clinical experts and fed back into the system. In some implementations, cryptocurrency tokens are used as the medium for financial transactions. In some implementations, the blockchain storing the outcome information is managed as a DAO, and NFTs on the blockchain correspond to outcome information. More details about the outcome information, the clinical outcome database, and implementations involving NFTs and/or a DAO, are described with respect to the system 200 of FIG. 2 and the system 600 of FIG. 6.

In some implementations, the medical test facilitator 102 performs various data mining operations on the outcome information in the outcome database, for example, to test for analytical validity, clinical validity, and clinical utility of the diagnostic tests. In this context, analytical validity refers to how well a genomic test predicts the presence or absence of a particular gene or genetic change. In other words, the extent to which the genomic test accurately detects whether a specific genetic variant is present or absent. For example, the administrator 108 can execute, on the server 104a, data-mining software, which uses a combination of test results, patient data and clinical outcome information in the clinical outcome database to test for analytical validity, clinical validity, and clinical utility of diagnostic genomic tests. In some implementations, the data mining software implements artificial intelligence (AI) algorithms.

In some implementations, the results or output of the data mining operations are stored in a health database that is proprietary to the medical test facilitator 102. For example, in such cases, the medical test facilitator 102 maintains the health database in one of the databases 106a-106e. In some implementations, the medical test facilitator 102 makes the data mining output information can be put back into 106a claims database and or available to interested stakeholders, for example, organization 142a or 142b, in exchange for financial compensation. In some implementations, cryptocurrency tokens are used as the medium for financial transactions. More details about the data mining operations and the health database are described with respect to the system 200 of FIG. 2.

Figure 2:
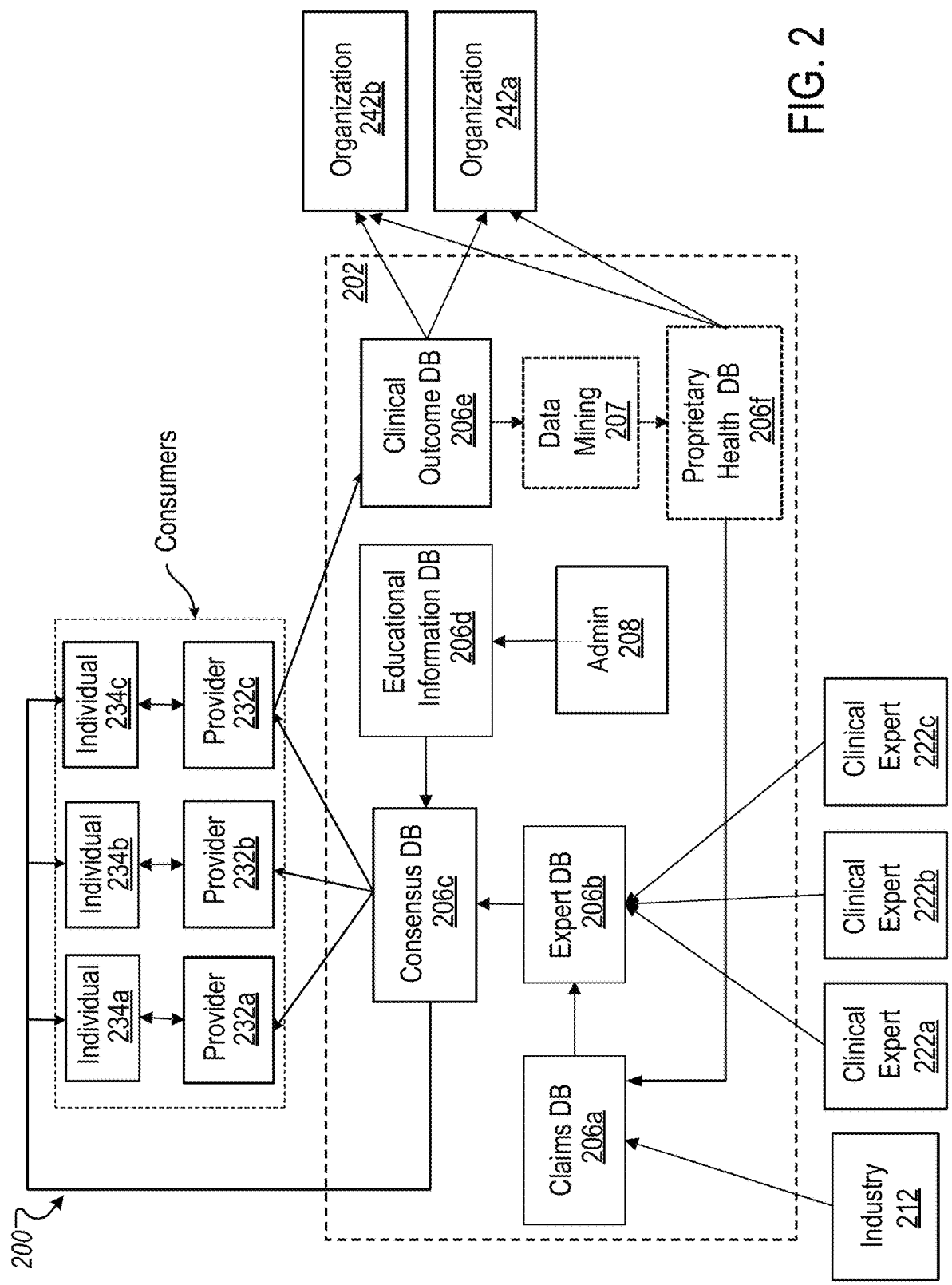
FIG. 2 illustrates a block diagram of a system that provides a distributed medical testing framework.

FIG. 2 illustrates a block diagram of a system 200 that provides a distributed medical testing framework. In some implementations, the system 200 is similar to the system 100, for example, the system 200 is a block diagram schematic of components of the system 100. The system 200 includes a medical test facilitator 202, industry participant 212, one or more clinical experts 222a, 222b and 222c (collectively, clinical experts 222a-222c), one or more medical providers 232a, 232b and 232c (collectively, medical providers 232a-232c) one or more individuals 234a, 234b and 234c (collectively, individuals 234a-234c), and one or more organizations 242a and 242b. The medical providers 232a-232c and individuals 234a-234c can be collectively referred to as consumers.

The medical test facilitator 202 provides the distributed medical testing informational framework. In some implementations, the medical test facilitator 202 is similar to the medical test facilitator 102. As shown, the medical test facilitator 102 includes a claims database (DB) 206a, an expert DB 206b, a consensus DB 206c, an educational information DB 206d, a clinical outcome DB 206e, a data mining module 207 and a proprietary health DB 206f. The systems and services of the medical test facilitator 202 are managed by one or more human operators, represented by administrator 208.

In some implementations, the industry participant 212 is similar to the industry participant 112a or 112b. For example, the industry 212 is a genomic test developer or genomic testing company in some cases. In some implementations, the industry participant 212, for example, a genomic testing company, makes clinical claims about specific screening or diagnostic genomic tests; each test may produce two or more possible results, and the results have specific clinical interpretations for disease or health. The set of possible results includes "positive", "negative," or "no call" (for example, an ambiguous result due to technical or biological factors). The interpretation for a "positive" result can be a probability of a specific disease. There can be known patient subgroups that tend to produce anomalous results for the genomic test.

In some implementations, the genomic testing company creates genomic test kits for particular consumer genomic tests, and includes clinical claims or interpretations in "package inserts" with the kits that describe the usage and interpretation of the associated genomic test kits. Many medical providers (for example, those without specialized genomic testing knowledge, such as in facilities that do not have in-house genetic counselors or qualified physicians) rely on the company's package inserts to interpret test results.

In some implementations, the industry participant 212 submits clinical claims about a genomic test to the medical test facilitator 202, for example, by uploading the clinical claims to the claims DB 206a, either by the industry participant 212 itself or the administrator 208. In some implementations, the claims DB 206a is similar to the claims database described with respect to the system 100. In some implementations, the claims DB 206a includes a blockchain, and the clinical claims are uploaded as one or more transactions of the blockchain. In some implementations, the claims DB blockchain is a private or semi-private blockchain. In such cases, industry participants who are authorized by the medical test facilitator 202, for example, based on approval by the administrator 208, are enabled to upload clinical claims as transactions in the claims DB blockchain. In some other implementations, the claims DB blockchain is a public blockchain where any industry participant can submit transactions.

In some implementations, for example, when the claims DB blockchain is used, the industry participants are reimbursed for submission of their clinical claims using cryptocurrency tokens. In some implementations, the industry participants are reimbursed for their clinical claims using other forms of transactions (e.g., other forms of financial transactions). In some implementations, no such reimbursement mechanism is used.

In some implementations, the uploaded clinical claims data is constrained to a specific format. For example, the specific format can define one or more fields corresponding to types of data that may and/or must be included in the clinical claims data. For example, the fields can correspond to a test make, model and/or version of the corresponding genomic test, a set of possible results of the test, and/or the claimed interpretation of each result, including probabilities or ranges of probabilities, and cases which can lead to possible anomalous results.

Each genomic test has at least one unique internal test identifier as a key throughout the distributed medical testing framework. For example, in some implementations an identifier is provided by the medical test facilitator 202, by an administrative or regulatory agency, or by another entity. A product identifier is an identifier associated generally with a genomic test. A device identifier is associated with a specific instance of a genomic test, such as particular kit used to administer the test to an individual patient. For example, the device identifier can be printed on a test kit and be scannable to identify the test kit and a genomic test performed using the test kit. One or more identifiers can be included in various types of stored data, as described throughout this disclosure. For example, in some implementations a blockchain transaction associated with a genomic test includes one or more identifiers associated with the genomic test. For example, one or more of a blockchain transaction storing clinical claim data about a genomic test in the claims DB 206a, a blockchain transaction storing an expert assessment of the genomic test in expert DB 206b, a blockchain transaction storing an expert consensus about the genomic test in consensus DB 206c, a blockchain transaction storing educational information about the genomic test in education information DB 206d, a blockchain transaction storing clinical outcome information and patient information in clinical outcome DB 206e, or a blockchain transaction storing results of data analysis about the genomic test in proprietary health DB 206f, can include a product identifier of the genomic test and/or a device identifier identifying a particular device used to administer the genomic test. For example, for the clinical outcome DB 206e, the identifier can be a device identifier of the specific test kit used to obtain the clinical outcome information of the blockchain transaction.

Identifiers can instead or additionally be associated with particular consumers or other entities. For example, a blockchain transaction storing an expert assessment of the genomic test can include an identifier corresponding to the expert providing the assessment. As another example, a blockchain transaction storing patient outcome data can include an identifier corresponding to the patient.

In some implementations, at least some information uploaded to the claims DB 206a is based on data in the clinical outcome DB 206e, described in further detail below. For example, as a result of data mining 207 based on outcome data in the clinical outcome DB 206e, clinical claims data (or updates thereto) can be determined, and data is included in (e.g., uploaded to) the claims DB 206a that includes the determinations of the data mining 206. For example, based on data mining 207 performed on the outcome data in clinical outcome DB 206e, it can be determined that a particular patient characteristic tends to cause anomalous results for a given genomic test. Data indicative of the particular patient characteristic and its linkage to anomalous results for the given genomic test is stored in the claims DB 206a for access, e.g., by experts.

In some implementations, the medical test facilitator 202 forwards the clinical claims from the claims DB 206a to the expert DB 206b for assessment by clinical experts. In some implementations, the expert DB 206b is similar to the expert database described with respect to the system 100. Clinical experts 222a-222c evaluate the clinical claims in the expert DB 206b that were submitted from the claims DB 206a. In some implementations, one or more of the clinical experts 222a-222c is similar to the clinical experts 122a-122c, and the notification of availability of the clinical claims to the clinical experts 222a-222c, and their subsequent assessment of the clinical claims, is done in a manner similar to that described with respect to the system 100.

In some implementations, based on their respective individual assessments, the clinical experts submit transactions into an expert DB blockchain. In some implementations, each assessment either accepts or rejects the clinical claims for a specific genomic test. In some implementations, the expert DB blockchain is a consortium-type blockchain. In such implementations, in addition to the medical test facilitator 202, the clinical experts 222a-222c, and/or their respective organizations, have management abilities to manage the blockchain. Entities authorized by the medical test facilitator 202 or the clinical experts 222a-222c are able to upload transactions into the blockchain. In some other implementations, the expert DB blockchain is a private blockchain. In such cases, clinical experts who are authorized by the medical test facilitator 202, for example, based on approval by the administrator 208, are enabled to upload assessments as transactions in the expert DB blockchain. In some other implementations, the expert DB blockchain is a public blockchain where any clinical expert can submit transactions. In some implementations, for example, when the expert DB blockchain is used, the clinical experts are reimbursed for their assessments using cryptocurrency tokens. In some other implementations, the clinical experts are reimbursed for their assessments using other forms of financial transactions, or using some other kind of transaction.

In some implementations, along with the assessments, experts 222a-222c submit, to the expert DB 206a, statistical summaries of test results and clinical actions taken for specific results of specific tests, for example, what percentage of the time a given clinical action was taken for a given result for the test. Such information is independent of any individual patient data.

In some implementations, the assessment of clinical claims corresponding to a genomic test by a clinical expert has one of several possible results. The possible results include, for example, explicit acceptance or rejection assessments based on expert knowledge, experience or clinical guidelines.

The possible results also include explicit acceptance or rejection assessments based on statistical analysis of internal clinical records. In such cases, tools for the statistical analysis, for example, algorithms or software, can be provided by the clinical experts themselves or by the medical test facilitator 202. In some cases, the statistical analysis yields a summary of test results, for example, the frequency of positive, negative, ambiguous and anomalous results, and clinical actions taken for each result.

The possible results also include reporting of a statistical summary of clinical actions taken for specific results for the genomic test, with no explicit acceptance or rejection assessments. In such cases, the medical test facilitator uses statistical tools that test whether the actual clinical actions taken match the probabilities in the clinical claim to generate an acceptance or rejection assessment of the clinical claim.

In some implementations, when a clinical expert, for example, one of clinical experts 222a-222c, uploads a transaction to the expert DB 206b, either accepting or rejecting a clinical claim for a specific genomic test, the upload triggers a consensus-testing mechanism in the medical test facilitator 202. For example, computing servers in the medical test facilitator, such as server 104a described with respect to the system 100, runs one or more software tools that evaluate an aggregate of acceptance or rejection assessments from one or more of the clinical experts 222a-222c. In some implementations, the assessments are weighted with suitable weights before evaluating with the software tools. The weights include, for example, recency of an assessment, level of expertise of the clinical expert, or sample sizes, among others. In some implementations, negative assessments (for example, rejections) are accorded higher weight compared to positive assessments (for example, acceptances).

In some implementations, the result of the evaluation of the assessments is compared to one or more preselected thresholds for acceptance and quorum size. The server running the consensus-testing tools, for example, server 104a, then uploads the result of the evaluation to the consensus DB 206c. In some implementations, the consensus DB 206c is similar to the consensus database described with respect to the system 100. In some implementations, in addition to the results of the evaluation, the server uploads the clinical experts' recommended clinical action for a positive, negative, ambiguous or anomalous result, along with the summary of relevant clinical data.

In some implementations, the server uploads the result of the evaluation as a transaction into a consensus DB blockchain, where the transaction either validates or refutes the interpretation provided by the clinical claims for that specific genomic test. In some implementations, the consensus DB blockchain is a private blockchain. In such cases, entities who are authorized by the medical test facilitator 202, for example, the administrator 208, are enabled to upload evaluations as transactions in the consensus DB blockchain. In some other implementations, the consensus DB blockchain is a public blockchain where any entity can submit transactions.

In some implementations, supporting educational information is provided to interpret specific genomic diagnostic tests manufactured by different genomic testing companies. Such educational information can be prepared by certified genetic counselors, and submitted to the consensus DB 206c by the medical test facilitator 202. Material for the educational information can be drawn, for example, from scientific/medical literature, regulatory guidance, recommendations of professional medical societies and expert opinion, among others. The educational information for a genomic test can include technical descriptions of the platform for the genomic test, functional biological basis for the genomic test, or technical or biological factors that lead to "no calls", among others. For example, there can be general limitations regarding the applicability of the genomic test to certain patient populations that can lead to anomalous results; this information will be provided in the educational material.

In some implementations, the educational information is added to the educational information DB 206d. In some implementations, the educational information DB 206d is similar to the educational database described with respect to the system 100.

In some implementations, the educational information is added as transactions to a blockchain maintained by the educational information DB 206d. In some implementations, the educational information DB blockchain is a private blockchain. In such cases, entities who are authorized by the medical test facilitator 202, for example, the administrator 208, are enabled to upload descriptions, information, or evaluations, as transactions in the educational information DB blockchain. In some other implementations, the educational information DB blockchain is a public blockchain where any entity can submit transactions.

In some implementations, the consensus DB 206c includes current statuses for available genomic tests that have assessed by clinical experts and submitted from the expert DB 206b. The current statuses include, for example, one or more of: (i) accepted/rejected status of the genomic testing company's clinical claims; (ii) recommended clinical action for positive, negative, ambiguous or anomalous results; (iii) summaries of relevant clinical data; or (iv) relevant educational information to understand the interpretation of genomic tests.

As described previously with respect to the system 100, an online portal hosted by the medical test facilitator 202 provides an interface to the consensus DB 206c, such that the consensus DB 206c can be accessed globally by individuals and participating medical providers, for example, individuals 234a-234c and medical providers 232a-232c. In some implementations, the online portal is a blockchain-based browser, or a general web browser. In this manner, consumers have access to clinical expert assessments, recommended clinical action and educational materials to guide their respective patients regarding consumer genomic tests.

In some implementations, for example, when the consensus DB blockchain is used, the consumers pay the medical test facilitator 202 for the assessments and the evaluations using cryptocurrency tokens. In some other implementations, the consumers pay the medical test facilitator 202 using other forms of financial transactions, or using some other kind of transaction.

In some implementations, consumers (for example, individuals 234a-234c and/or medical providers 232a-232c, with the consent of their respective patients), upload clinical outcome data regarding the clinical or analytical validity and clinical utility of individual genomic tests to the clinical outcome DB 206e. In some implementations, as described in more detail below, the uploaded clinical outcome data is associated with an NFT. In some implementations, the clinical outcome DB 206e is similar to the clinical outcome database described with respect to the system 100. Uploading of the clinical outcome data is optional in some cases; there is no requirement for the medical providers or the patients to provide the information, except as an optional voluntary submission. However, consumers who upload the clinical outcome data can be reimbursed for sharing the information in some cases, as described in greater detail below.

In some implementations, the clinical outcome data includes reports of test results with actual clinical outcomes. Such information allows determination of true and false positive rates, and the subsequent calculations of sensitivity, specificity, positive predictive value (for example, precision), negative predictive value, accuracy, and other useful metrics for determining the predictive value of a genomic test. In some implementations, the clinical outcome data also includes details of patient information, such as personal characteristics (for example, age, gender, and/or other demographic data), disease states (for example, diabetes, etc.), genetic variations (for example, known chromosomal anomalies or single-nucleotide polymorphisms), imaging (for example, MRIs or ultrasounds characterizing the patient), and other relevant information for further downstream data mining. Due to the sensitive nature of the patient information, the medical test facilitator 202 uses stringent data handling protocols and strong security to secure the data in the clinical outcome DB 206e.

Interested stakeholders, for example, one or more of organizations 242a or 242b, can access the clinical outcome data from the clinical outcome DB 206e by logging in through the online portal. The clinical outcome data is useful to stakeholders, since the results can serve as a post-market validation of consumer genomic tests, which are largely unregulated or not subjected to rigorous clinical trials. Access to post-market data for specific tests can allow for re-evaluations of test efficacy and help medical providers accurately inform their patients. In some implementations, one or more of the organizations 242a or 242b are similar to the organizations 142a and/or 142b described with respect to the system 100.

Figure 6:
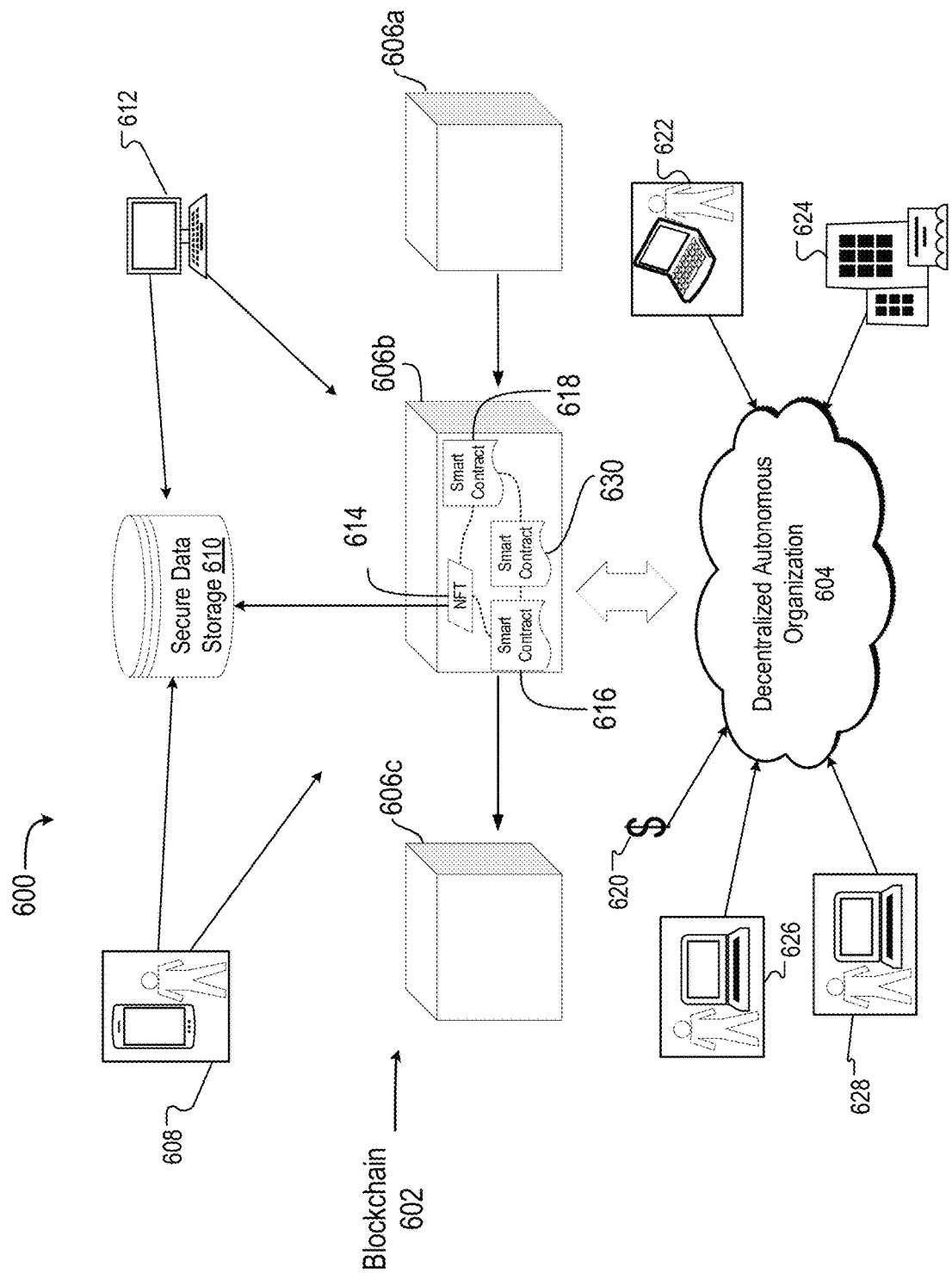
FIG. 6 illustrates a block diagram of a system that provides medical data access.

In some implementations, the clinical outcome DB 206e is implemented as, or in association with, a blockchain. Clinical outcome data, patient information, and other data can be uploaded as transactions in the blockchain and/or can be stored off-blockchain and associated with on-blockchain records such as NFTs. For example, as shown in FIG. 6, a medical data system 600 includes a blockchain 602. The blockchain 602 includes a plurality of blocks, such as blocks 606a, 606b, 606c. Each block in the blockchain includes a hash value based on cryptographic hash operations on previous blocks, so that the blockchain 602 as a whole provides an immutable record. In this example, the medical data system 600 also includes a secure data storage 610 that can be external to the blockchain 602. The secure data storage 610 holds private data such as clinical outcome data and patient information and, accordingly, is at least partially access-controlled. For example, access to data of the secure data storage 610 can require entry of credentials. In some implementations, the secure data storage 610 is similar to the clinical outcome DB 206e and/or to the clinical outcome database described with respect to the system 100. In some cases, the secure data storage 610 can be the clinical outcome DB 206e. Data stored in the secure data storage 610 can have any or all of the characteristics of data stored in the clinical outcome DB 206e, as described elsewhere in this disclosure. For example, the secure data storage 610 can be managed by a medical test facilitator (e.g., the medical test facilitator 202), and access to the secure data storage 610 can be restricted to entities authorized by the medical test facilitator. In some implementations, the secure data storage 610 is a private blockchain. Entities who are authorized by the medical test facilitator 202 (e.g., consumers or organizations approved by the administrator 208) are enabled to upload outcome results or patient information, or both, as transactions, or to access the uploaded transactions, in the secure data storage 610. In some other implementations, the secure data storage 610 is a public blockchain, distinct from the blockchain 602, where any entity can submit or access transactions; however, some transactions may be stored in encrypted form to retain data access controls.

In some implementations, clinical outcome data and patient information are stored as a transaction in a blockchain of the secure data storage 610, and the transaction includes one or more identifiers of the genomic test corresponding to the clinical outcome data. For example, the identifiers can include a device identifier of the specific genomic test administered, a product identifier that identifies the genomic test generally, or both.

In some implementations, the secure data storage 610 is integrated into the blockchain 602, and need not represent a separate storage/database. For example, clinical outcome data and patient information in the secure data storage 610 can be stored in encrypted form in blocks of the blockchain 602, and an on-blockchain encryption scheme, such as symmetric or asymmetric key encryption, can be used to restrict access to the encrypted data.

Consumers 608 (such as individuals and/or medical providers, as described above) can upload clinical outcome data and patient information to the secure data storage 610. For example, consumers 608 can access a website or application (e.g., mobile application) that interfaces with the blockchain 602 and the secure data storage 610 (those being integrated into a combined database in some implementations). Using the website or application, individuals are able to upload their own clinical outcome data and patient information. In some implementations, medical providers can use the website or application to upload their patients' clinical outcome data and patient information, conditional on permission from the patients. In some implementations, medical providers can use the website or application to upload clinical outcome data and patient information that has been stripped of personally-identifying information such as name and address, such that the patient corresponding to the data cannot be identified.

Entities 612 can use the same or another website or application to obtain data from the secure data storage 610. For example, entities 612 can pay a data access fee to the medical test facilitator and, in exchange, be provided with clinical outcome data and patient information, so as to perform analyses and data mining. The entities can include the organizations 242a, 242b, the industry participant 212, and/or other entity types.

In some implementations, individual clinical outcome data and patient information in the secure data storage 610 are associated with NFTs, where an NFT is a unit of data (e.g., a unique unit of data) stored on the blockchain 602. For example, as shown, data for some particular individual clinical outcome and corresponding patient information are associated with an NFT 614 stored in block 606b in the blockchain 600. The NFT 614 is owned by one or more accounts on the blockchain 602 (e.g., by one or more entities having corresponding accounts on the blockchain 602), and ownership information (both current ownership and ownership history) is written into one or more blocks of the blockchain 602, such that ownership of the NFT 614 is confirmed by consensus operations of the blockchain 602. An immutable mapping exists between the owning account(s) and the NFT 614.

As mentioned above, the NFT 614 is associated with particular data in the secure data storage 610 to which ownership of the NFT 614 provides access. For example, in some implementations the NFT 614 includes (e.g., stores) a link to the particular data in the data storage 610. In some implementations, the NFT 614 includes an identifier of the particular data and/or of a location at which the particular data is stored in the secure data storage 610, such as a block and location therein when the secure data storage 610 is implemented as a blockchain, or storage index information for the particular data in the secure data storage 610.

Creation of the NFT 614 can coincide with storage of the corresponding particular clinical outcome data and/or particular patient information in the secure data storage 610. For example, when a consumer 608 operates a website or application to store the particular data, the website or application also interfaces with the blockchain 602 to create and store the NFT 614 that corresponds to the stored particular data. Creation of the NFT 614 can include invoking an appropriate contract operation of a smart contract 618 that generates and stores the NFT 614 on the blockchain 602.

An owner of the NFT 614 can use the NFT 614 to access the corresponding particular data in the secure data storage 610. For example, in some implementations, the owner of the NFT 614 (e.g., an entity 612) can invoke execution of a contract operation of a smart contract 616 in the blockchain 602. Invoking can include running an on-blockchain command such as RETRIEVE_DATA (198LL26A), where "RETRIEVE_DATA" corresponds to the smart contract 616 and "198LL26A" is an identifier of the NFT 614. The smart contract 616 confirms that the initiator of the execution is an authentic owner of the NFT 614, e.g., as recorded in one or more blocks of the blockchain 602. If so, the smart contract 616 retrieves the particular data corresponding to the NFT 614 from the secure data storage 610 (external to the blockchain 602 or included in the blockchain 602), and provides the particular data to the initiator. The smart contract 616 can identify the particular data corresponding to the NFT 614 by identifying the link or other identifier of the particular data in the NFT 614.

In some implementations, if the invoker of the contract operation is not an owner of the NFT 614, the smart contract 614 does not provide the corresponding particular data, maintaining data privacy and access security. In some implementations, the smart contract 614 provides the particular data to authentic owners in encrypted form, such as encrypted by a public key of the authentic owner; only the authentic owner, using their private key, is able to decrypt the encrypted data and access the corresponding particular data.

Incorporation of NFTs into the system 600 (and, in some implementations, into the systems 100 and 200) allows for (i) efficient compensation for data provision, and (ii) secure monetization of medical data to improve overall data access efficiency. In some implementations, when the NFT 614 is created, the consumer or organization who provided the medical data corresponding to the NFT 614 can be provided with a sum of money or cryptocurrency, to compensate the consumer for providing the medical data. For example, in some implementations the smart contract 618 that creates the NFT 614 is also configured to transfer a predetermined amount of cryptocurrency (e.g., Bitcoin, Ethereum, Litecoin, Dogecoin, or some other suitable cryptocurrency specific to the blockchain 602) to a blockchain account corresponding to the consumer, upon creation of the NFT 614. For example, the compensation can be provided by the medical test facilitator 202 that may manage the secure data storage 610. Alternatively, or in addition, in some implementations the NFT 614, once created, is owned by the consumer who provided the medical data corresponding to the NFT 614. The consumer can subsequently sell the NFT 614 to one or more other accounts on the blockchain 602 in exchange for compensation such as cryptocurrency. The NFT 614 can be subsequently traded (sold) to and between accounts corresponding to various entities 612 that would like access to the corresponding data. Trading of the NFT 614 can be performed using one or more smart contracts that specify gas fees and otherwise regulate allowed trades. Accordingly, medical data can be provided efficiently to those entities willing to pay the highest compensation for the NFT 614 corresponding to the medical data.

NFT transactions can be organized in a data warehouse browsable by entities seeking medical data. The data warehouse can be implemented as a website or application and can interface with the secure data storage 610 and blockchain 602. Entities can use the data warehouse to search for specific types of medical data desired, such as clinical outcome data correlated with particular demographic or disease characteristics of patients.

In some implementations, operations of the blockchain 602, such as the operations performed by smart contracts of the blockchain 602 (e.g., smart contracts 616, 618), are regulated by a decentralized autonomous organization (DAO) 604. The DAO 604 is a transparent, distributed consortium of stakeholders (as defined by ownership of tokens, such as tokens stored on the blockchain 602) that collectively set parameters of the blockchain 602. Governance operations of the DAO 604 can be conducted on the blockchain 602. As shown in FIG. 6, the stakeholders (e.g., members of the DAO 604) can include, for example, investors 620, developers 622, founders 624, individuals 626, and medical providers 628. The founders 624 conceptualize the DAO 604 and its governance rules, mint a first round of tokens that are retained by the founders 624, and recruit members to the DAO 602. In some implementations, the founders 624 include the medical test facilitator 202. The investors 620 contribute funds or infrastructure to the DAO 604 and are compensated with tokens. Developers 622 code smart contracts of the blockchain 602; create websites, applications, and other interfaces to the secure data storage 610 and/or blockchain 602; develop analysis tools such as AI-based data models and prediction algorithms; and work on other technical aspects of the DAO 604, blockchain 602, and related systems. The developers 622 are compensated with tokens. Individuals 626 and medical providers 628 can be compensated in tokens of the DAO 604 for providing medical data to the secure data storage 610, for participating in clinical trials, and for other reasons.

Ownership of tokens allows participation in consensus operations of the DAO 604. Decisions are made by voting, with vote weights proportional to tokens held by each member of the DAO 604. The tokens are limited in number and are specific to the blockchain 602. For example, in some implementations, a plurality of tokens that are labeled "MedDataTokens" are created and used for the blockchain 602. The DAO 604 is itself governed by a public smart contract (e.g., an open-source smart contract 630 on the blockchain 602) to provide transparency to decision-making by the DAO 604. Voting by members and decisions of the DAO 604 are logged in the blockchain 602 and are visible to other members of the DAO 604. The votes define operations of the blockchain 602, such as content of one or more smart contracts on the blockchain 602. For example, the DAO 602 can collectively determine parameters such as a compensation amount for providing medical data to the secure data storage 610, by configuring parameters of the smart contract 618; rules governing ownership and transfer of NFTs on the blockchain 602, such as whether NFTs can be owned by multiple accounts and the amounts of fees extracted when NFTs are traded, by configuring parameters of a smart contract used for NFT trading; rules governing medical data access, such as type(s) of encryption used, by configuring parameters of the smart contract 616; and/or rules governing who is permitted to provide medical data to the secure data storage 610, by configuring parameters of the smart contract 618. For example, in some implementations each NFT transaction in the blockchain 602 incurs a small fee that is split among holders of the tokens of the DAO 604. This incentivizes participation in the DAO 604 and rewards the founders 624 and other stakeholders for organizing the DAO 604. The fee is set in a smart contract invoked to trade NFTs, and the smart contract can be edited to change the fees using a consensus operation of the smart contract 630.

The DAO 604 can provide various benefits that improve medical data provision. For example, in some implementations the DAO 604 facilitates concerted action by consumers (e.g., individuals and medical providers) to collectively impose desired parameters of the blockchain 602, such as high levels of data privacy (e.g., high anonymity requirements of data stored in the secure data storage 602) and high levels of reimbursement to providers of the medical data. The DAO 604 can also facilitate cooperation between different types of entities. For example, research organizations that are members in the DAO 604 can provide opportunities to consumer members of the DAO 604 to participate in clinical trials; terms of the clinical trials can be enforced by collectively-governed smart contracts on the blockchain 602. Because the DAO 604 can be accessed anonymously and can be publicly monitored, users (e.g., patients) can feel comfortable participating in data exchange and trading without revealing their personally identifying data, and gain trust in organizations that participate in the DAO 604. The DAO 604 also facilitates communication and interaction between members, such as to form communities targeting particular health-related issues (e.g., sharing experiences regarding a specific disease).

In some implementations, for example, when the clinical outcome DB blockchain is used, the medical providers and/or their patients are reimbursed by the medical test facilitator 202 for uploading the clinical outcome data, using cryptocurrency tokens. The organizations 242a and/or 242b, in turn, pay the medical test facilitator 202 for the ability to access the clinical outcome data from the database, using cryptocurrency tokens. In other implementations, the consumers medical providers are reimbursed by the medical test facilitator 202 using other forms of financial transactions, or using some other kind of transaction. Similarly, the organizations pay the medical test facilitator 202 using other forms of financial transactions, or using some other kind of transaction. These compensation mechanisms do not require (though can include) an NFT component.

Referring again to FIG. 2, in some implementations, the medical test facilitator 202 performs further analysis of the clinical outcome data in the clinical outcome DB 206e. In some cases, the analysis is on large patient populations. In some cases, computer servers of the medical test facilitator 202, for example, server 104a, use software tools in the data mining module 207 to analyze the data.

In some implementations, the data mining module 207 uses a combination of test results, patient data and clinical outcomes in the clinical outcome DB 206e to test for analytical validity, clinical validity, and clinical utility of the diagnostic tests. For example, in such cases, the data mining determines how accurately and reproducibly the genomic test generates a useful clinical action on the population of participating patients. In some cases, advanced data mining is used to find patterns of covariates within the patient data (for example, body mass index (BMI) or age, among others) that may lead to anomalous test results.

In some implementations, the software tools employed by the data mining module 207 use artificial intelligence (AI) algorithms. The AI algorithms can be used for pattern recognition and deep learning. For example, the AI algorithms can perform deep analysis of complex patterns, for example, patient genetics or imaging results, incorporating data from public or private/proprietary databases with population genetics, or large scale imaging repositories.

In some implementations, the medical test facilitator 202 stores the results of the data mining analyses in the proprietary health DB 206f. In some implementations, the proprietary health DB 206f is similar to the health database described with respect to the system 100. Interested stakeholders, for example, one or more of organizations 242a or 242b, can access the data mining results from the proprietary health DB 206f by logging in through the online portal. In some implementations, the organizations 242a and/or 242b pay the medical test facilitator 202 using cryptocurrency tokens for the ability to access the results from the database. In other implementations, the organizations pay the medical test facilitator 202 using other forms of financial transactions, or using some other kind of transaction. In some implementations, the proprietary health DB 206f can be structured as described for the secure data storage 610, with data mining results corresponding to blockchain-stored NFTs that are tradable to transfer access to the data mining results.

In some implementations, instead of or in addition to storage in the proprietary health DB 206f, the medical test facilitator 202 stores the results of the data mining analyses in the claims DB 206a. In such cases, the results constitute new information about one or more genomic tests corresponding to the results, and a re-analysis of the genomic tests can be performed, e.g., via the expert DB 206b.

Use of blockchains to store transactions in one or more databases, for example, the claims DB 206a, expert DB 206b, consensus DB 206c or clinical outcome DB 206e, among others, allow multiple independent stakeholders to enter information into the system, with conflicts in the information being resolved by the blockchains. However, although different stakeholders can submit information and evaluations into various databases independently, the overall medical testing framework can be tightly controlled by the medical test facilitator 202, for example, by use of private or semi-private blockchains in some implementations. However, in some implementations, blockchains can be publicly managed, such as by a DAO 604 as described above.

Blockchains also enable realization of a "trustless" system with no overall arbiter. The summary evaluation of genomic test derives from a consensus of clinical expert assessments, implemented using automated software tools that follow pre-set evaluation algorithm(s). The clinical claims, clinical expert assessments, and evaluations that form the basis of the consensus DB 206d are immutable and auditable when blockchains are used, which provides a permanent and traceable trail of medical accountability.

Using blockchain in the clinical outcome DB 206e for outcome analysis enables medical providers or patients to anonymously provide personal information, have ownership of their clinical outcome data and feel empowered to be reimbursed for providing the data in a secure mechanism (for example, using cryptocurrencies) without requiring assistance of a third party.

Figure 3:
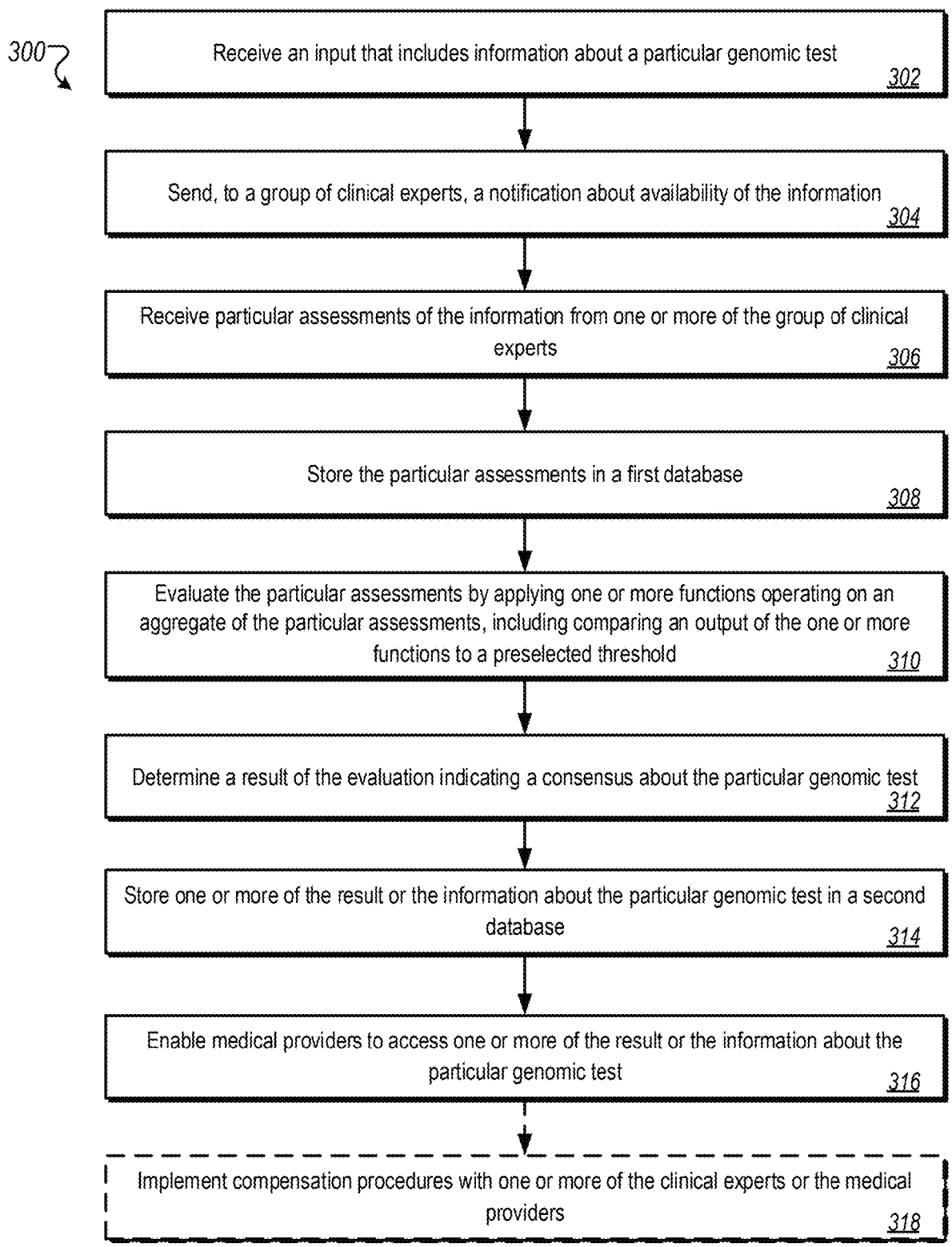
FIG. 3 illustrates an example of a process to provide geographically distributed access to a genomic test using a distributed medical testing framework.

FIG. 3 illustrates an example of a process 300 to provide geographically distributed access to a genomic test using a distributed medical testing framework. In some implementations, the process 300 is performed by components of the medical test facilitator 102 (or equivalently, medical test facilitator 202), for example, by the server 104a, to coordinate access to consumer genomic tests and expert assessments of clinical claims corresponding to the consumer genomic tests that are managed by the medical test facilitator 102. Accordingly, the following sections describe the process 300 with respect to the server 104a. However, the process 300 also may be performed by other devices.

In some implementations, the process 300 is performed by the server 104a by executing one or more instructions that are stored in memory, for example, hard drive storage or flash memory, coupled to the server. One or more processors included in the server 104a execute these instructions to perform the operations of the process 300 that are described below.

The process 300 starts when the server receives an input that includes information about a particular genomic test (302). For example, industry participant 112a or 112b accesses the online portal hosted by the medical test facilitator 102 and uploads information about a genomic test, including clinical claims about the genomic test made by the industry participant 112a or 112b. As another example, an authorized representative of the medical test facilitator 102, e.g., an authorized medical geneticist or the administrator 108, uploads the information about the genomic test. Server 104a, which hosts the web server for the online portal, receives the information uploaded by the industry participant and stores the information in the claims database, for example, claims DB 206a. To illustrate with an example of a particular genomic test, without loss of generality, a genomic testing company (for example, industry participant 112a or 112b) can provide a set of screening tests, including a non-invasive test for "Down syndrome" in a fetus using a pregnant woman's blood. This particular test can detect an extra copy of chromosome 21 in the fetus by analyzing the circulating DNA in the mother's blood. The company may claim that their "Down syndrome" test is sufficiently sensitive and specific enough to quantitate the DNA originating from the fetus, and that the test accurately assesses the probability of the fetus having Down syndrome. The company may claim that a positive test will result in the fetus having Down syndrome 99% of the time. The information about the particular test, including the claims made by the company, are uploaded to the server 104a.

The server sends, to a group of clinical experts, a notification about availability of the information (304). For example, the server 104a forwards the clinical claims about the genomic test to the expert database, for example, expert DB 206b, and sends a notification to one or more clinical experts 122a-122c about the availability of the new genomic test and the corresponding clinical claims. Continuing with the illustrative example of the particular genomic test described above, the server 104a sends a notification to several clinical experts with information about the Down syndrome test and the claims about the test from the genomic testing company.

The server receives particular assessments of the information from one or more of the group of clinical experts (306). For example, following the notification from the server, one or more of the clinical experts accesses the clinical claims about the new genomic test from the claims database, analyzes the clinical claims, and provides their individual assessments of the clinical claims. The clinical experts submit their individual assessments to the server 104a though the online portal. Continuing with the illustrative example of the particular genomic test described above, the clinical experts independently and anonymously evaluate the claims about the Down syndrome test made by the genomic testing company, and either accept, reject or have no opinion on the claims. The clinical experts submit their individual evaluations to the server 104a.

The server stores the particular assessments in a first database (308). For example, the server 104a stores the individual assessments received from the clinical experts in the expert database, for example, expert DB 206b. As described previously, in some implementations, the assessments are stored as transactions in a blockchain. Continuing with the illustrative example of the particular genomic test described above, the server 104a stores the individual evaluations of the claims about the Down syndrome test that are received from the clinical experts in the expert database 206b.

The server evaluates the particular assessments by applying one or more functions operating on an aggregate of the particular assessments, including comparing an output of the one or more functions to a preselected threshold (310). For example, the server 104a executes operations for one or more software tools that evaluate an aggregate of assessments from one or more of the clinical experts 122a-122c about the clinical claims for a genomic test. As described previously, in some implementations, the assessments are weighted with suitable weights for the evaluation. In some implementations, the server 104a compares the result of the evaluation of the assessments to one or more preselected thresholds for acceptance and quorum size. Continuing with the illustrative example of the particular genomic test described above, once a quorum of expert evaluations is received for the claims about the Down syndrome test, the server 104a executes processes that use algorithms with weightings for various factors, which are performed on the aggregate set of evaluations from the clinical experts. The server 104a compares the result of executing the processes on the aggregate set of evaluations to a preset threshold consensus parameter.

The server determines a result of the evaluation indicating a consensus about the particular genomic test (312). For example, based on evaluating the aggregate of the clinical expert assessments and threshold comparison, the server 104a determines whether to accept or reject the clinical claims about a genomic test, or whether a determination cannot be made. Continuing with the illustrative example of the particular genomic test described above, the server 104 determines, following the threshold comparison of the result of the aggregate set of evaluations, a consensus evaluation of the validity of the claims about the Down syndrome test made by the genomic testing company.

The server stores one or more of the result or the information about the particular genomic test in a second database (314). For example, the server 104a uploads the result of the evaluation to the consensus database, for example, consensus DB 206c. In some implementations, in addition to the results of the evaluation, the server 104a uploads the clinical experts' recommended clinical action for a positive, negative, ambiguous or anomalous result, along with the summary of relevant clinical data. Continuing with the illustrative example of the particular genomic test described above, the server 104 determines, the server 104a uploads, to the consensus DB 206c, the consensus evaluation of the validity of the claims about the Down syndrome test made by the genomic testing company.

As described previously, in some implementations, the server uploads the result of the evaluation as a transaction into a consensus DB blockchain, where the transaction either validates or refutes the interpretation provided by the clinical claims for that particular genomic test. In some implementations, the server 104a also uploads, from the educational information database, for example, education information DB 206e, educational information corresponding to the particular genomic test, to help a medical provider understand the genomic test and related data.

The server enables consumers to access one or more of the result or the information about the particular genomic test (316). For example, the server 104a announces the availability of a new genomic test, including corresponding expert assessments of clinical claims, evaluation result of the assessments, and educational information about the genomic test. Based on the announcement, one or more consumers that are authorized by the medical test facilitator 102, for example, individuals 134a or 134b or for example medical providers 132a or 132b, can obtain the genomic test data from the consensus database 206c, and use the test data for their respective patients, for example, for patient screening, diagnostic or prognostic tests. Continuing with the illustrative example of the particular genomic test described above, when a patient presents genomic test results for the Down syndrome test to a medical provider who has no specialized knowledge, the provider may be unable to interpret the specific test without additional information. The medical provider can access the claims about the Down syndrome test made by the genomic testing company, and the consensus evaluation of the validity of these claims, from the consensus database 206c. In doing so, the medical provider can obtain the additional information to better care for the patient, by using the validated state-of-the-art interpretations of the claims about the particular genomic test.

Optionally, in some implementations, the server implements compensation procedures with one or more of the clinical experts or the consumers (318). For example, in some implementations, the industry participants and the clinical experts are reimbursed by the medical test facilitator 102 for providing the clinical claims and assessments, respectively. Continuing with the illustrative example of the particular genomic test described above, the medical test facilitator 102 compensates the clinical experts for providing their individual evaluations of the claims about the Down syndrome test made by the genomic testing company. The consumer also pays the medical test facilitator 102 for accessing the genomic test data from the consensus database.

In some implementations, for example, where blockchains are used for transactions in the system, the payments are made using cryptocurrencies. In some other implementations, the payments are made using other forms of financial instruments.

FIG. 4 illustrates an example of a process 400 to manage clinical outcomes for a genomic test using a distributed medical testing framework. In some implementations, the process 400 is performed by components of the medical test facilitator 102 (or equivalently, medical test facilitator 202), for example, by the server 104a, to coordinate reception and analysis of clinical outcome data for genomic tests directly from consumers, and making the clinical outcome data or corresponding data mining results, or both, to interested stakeholders. Accordingly, the following sections describe the process 400 with respect to the server 104a. However, the process 400 also may be performed wholly or partially by other devices, such as by smart contracts executing in blockchain databases.

In some implementations, the process 400 is performed by the server 104a by executing one or more instructions that are stored in memory, for example, hard drive storage or flash memory, coupled to the server. One or more processors included in the server 104a execute these instructions to perform the operations of the process 400 that are described below.

The process 400 starts when the server receives, from a particular consumer, particular patient data corresponding to administration of a particular genomic test on a particular patient (402). For example, one or more of the individuals 134a or 134b or medical providers 132a or 132b (with the consent of their respective patients) upload clinical outcome data regarding the clinical validity and/or clinical utility of a particular genomic test to the medical test facilitator 102 through the online portal hosted by the server 104a. Continuing with the illustrative example of the particular Down syndrome genomic test described above, a medical provider who accessed the information from the second database along with the patient who accessed the claims about the test made by the genomic testing company and the consensus evaluation of the validity of these claims from the consensus database 206c at (316) above, may provide feedback on the test results and its clinical manifestations for the patient of the medical provider. For example, the screening test indicated a positive result for Down syndrome and the expert consensus may be that under specific conditions, it was 99% probable that an infant with the particular genomic trait would have Down syndrome. Subsequently, an invasive gold-standard diagnostic test for Down syndrome for the patient may have confirmed the result of the screening test. In this case, the clinical outcome would be in agreement with the claims made by the genomic testing company for the particular genomic test. Such verification using real-world patient data is important for the evaluation of novel genomic tests, because data can be generated for large patient cohorts that enable analyzing the analytical validity (for comparison of different testing brands for a specific test), clinical validity (for correlation between the genomic marker and actual disease manifestation) and clinical utility (for effectiveness of a treatment based on the prognosis of the test result) for the genomic tests.

The server stores, in a third database, the particular patient data along with one or more other patient data corresponding to other administrations of the particular genomic test on other patients (404). For example, the server 104a stores the clinical outcome data uploaded by the consumer in the clinical outcome database, for example, clinical outcome DB 206e. The clinical outcome data is stored along with clinical outcome data received from other consumers for the same genomic test. Continuing with the illustrative example of the particular genomic test described above, the server 104a stores, in the clinical outcome DB 206e, the information provided by the consumer, which includes feedback on the test results, its clinical manifestations for the patient, and relevant data about the patient.

In some implementations, the third database includes or is communicatively coupled to a blockchain database. For example, the clinical outcome data is stored in the secure data storage 610 which is included in or communicatively coupled to blockchain 602. Storage can be performed by the server, directly by a provider of the clinical outcome data, or by a smart contract 618 of the blockchain 602. Continuing with the illustrative example of the particular genomic test described above, the consumer uses a mobile application to invoke execution of the smart contract 630. The smart contract 630 uploads clinical outcome data to the secure data storage 610. In some implementations, the smart contract 630 transfers cryptocurrency (a public cryptocurrency and/or a cryptocurrency token specific to the blockchain 602) to an account corresponding to the consumer.

In some implementations, the uploaded clinical outcome data is associated with an NFT on the blockchain 602. For example, the smart contract 630, as part of its execution, generates the NFT 614 on the blockchain 602, and the NFT 614 includes an identifier of the clinical outcome data. In some implementations, the NFT 614 is owned by the account corresponding to the consumer. The NFT 614 can subsequently be traded by the consumer, e.g., in exchange for cryptocurrency, so as to transfer access to the clinical outcome data. Continuing with the illustrative example of the particular genomic test described above, the consumer sells the NFT 614 to a third party (e.g., an organization) in exchange for cryptocurrency. The third party can invoke execution of the smart contract 616 to retrieve the clinical outcome data, conditional on the third party owning the NFT 614 (e.g., conditional on a blockchain account of the third party holding the NFT 614).

The server enables a third party to access patient data for the particular genomic test from the third database, e.g., upon authorization by an administrator (406). For example, interested stakeholders, for example, one or more of organizations 142a or 142b that are authorized by the medical test facilitator 102, are allowed to access the clinical outcome data from the clinical outcome database 206e by logging in through the online portal. Continuing with the illustrative example of the particular genomic test described above, the server 104a enables a third party with authorization by the administrator 108 to access the information provided by the consumer, for example feedback on the test results of the Down syndrome test or its clinical manifestations for the patient, so that outcomes of the particular genomic test can be analyzed. In some implementations, the third party is a party owning the NFT corresponding to the patient data, and the patient data is accessed through blockchain operations (e.g., smart contract execution) conditional on owning the NFT.

The server analyzes aggregate patient data, including determining, using the aggregate patient data, one or more clinical patterns corresponding to the particular genomic test (408). For example, the server 104a performs further analysis of the clinical outcome data received from various consumers for a particular genomic test. In some cases, amount of data is received for large patient populations. As described previously, the server 104a uses software tools in the data mining module 207 to analyze the data, which uses a combination of test results, patient data and clinical outcomes in the clinical outcome DB 206e to test for analytical validity, clinical validity, and clinical utility of the diagnostic tests. In some cases, advanced data mining is used to find patterns of covariates within the patient data. In some implementations, the software tools employed by the data mining module 207 use AI algorithms to perform deep analysis of complex patterns, for example, patient genetics or imaging results. Continuing with the illustrative example of the particular genomic test described above, the server 104a conducts outcome analysis using the information about the Down syndrome test from various consumers that are stored in the clinical outcome database 206, to evaluate the analytical validity, clinical validity and clinical utility of the particular test.

The server stores the analysis data in a fourth database (410). For example, the server 104a stores the results of the data mining analyses in the health database, for example, proprietary health DB 206f. In some implementations, the server 104a stores the analysis data as transactions in a blockchain in the health database. Continuing with the illustrative example of the particular genomic test described above, the server 104a stores the result of the outcome analysis about the Down syndrome test in the proprietary health DB 206f.

The server enables a third party to access patient data for the particular genomic test from the fourth database upon authorization by an administrator (412). For example, interested stakeholders, such as one or more of organizations 142a or 142b, are allowed, upon authorization by the medical test facilitator 102, to access the data mining results from the health database 206f by logging in through the online portal. Continuing with the illustrative example of the particular genomic test described above, the server 104a makes the result of the outcome analysis about the Down syndrome test stored in proprietary health DB 206f available to third parties upon authorization by the administrator 108.

Optionally, in some implementations, the server implements a compensation procedure with one or more of the particular individual or medical providers or the third party (414). For example, in some implementations, and individual or a medical providers and/or their patients are reimbursed by the medical test facilitator 102 for providing the patient data, for example, clinical outcomes of the genomic tests applied to the patients. The organizations also pay the medical test facilitator 102 for accessing the data mining results from the health database. Continuing with the illustrative example of the particular genomic test described above, the medical test facilitator 102 reimburses the medical provider or the patient of the medical provider, for providing the feedback on the test results of the Down syndrome test, its clinical manifestations for the patient, and relevant data about the patient. The medical test facilitator 102 charges third parties for accessing the information from the clinical outcome database 206e, or accessing the outcome analysis about the particular test from the health database 206f. In some implementations, for example, where blockchains are used for transactions in the system, the payments are made using cryptocurrencies. In some other implementations, the payments are made using other forms of financial instruments.

Figure 5:
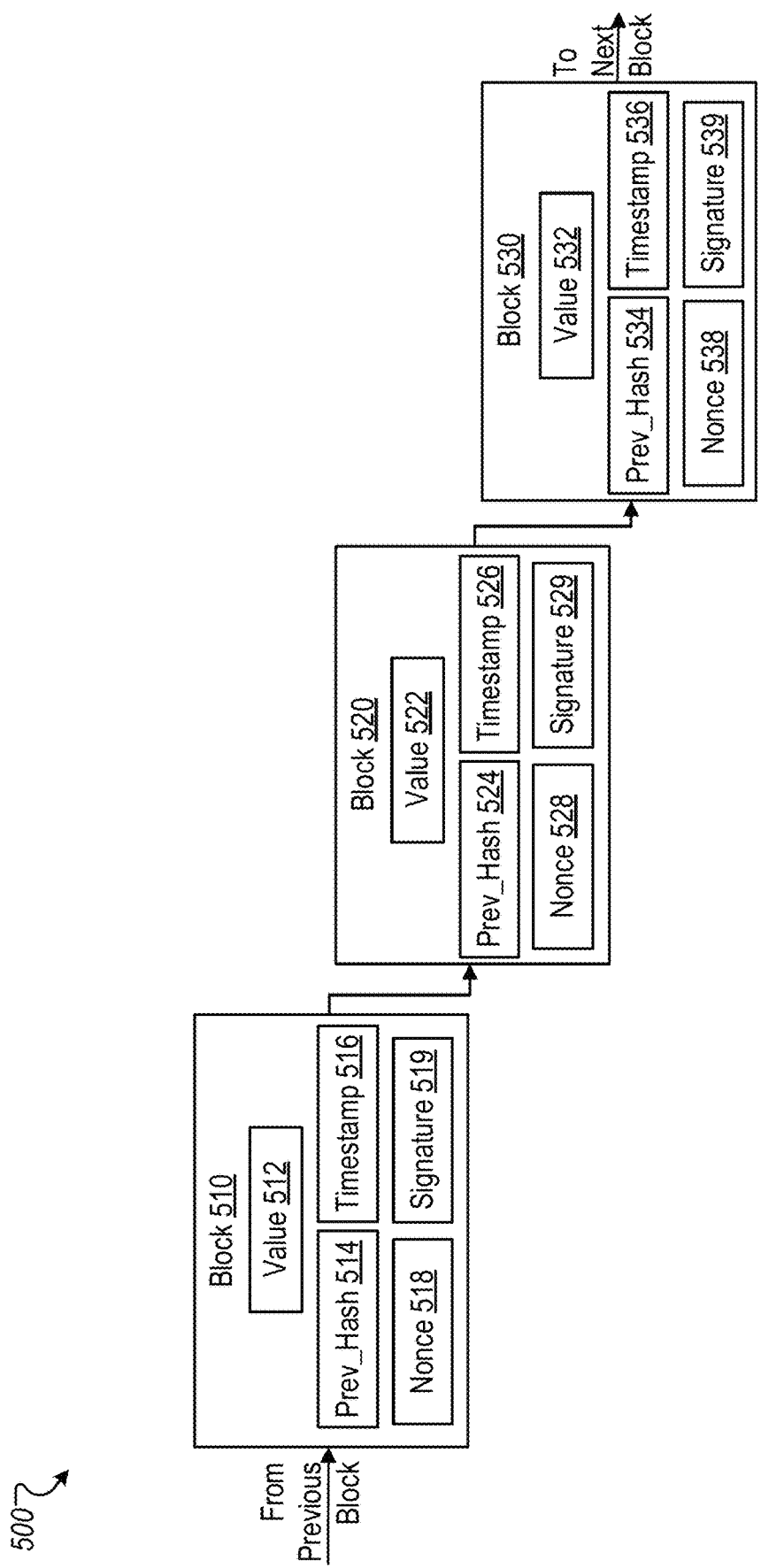
FIG. 5 illustrates an example of a portion of a blockchain for use in a distributed medical testing framework.

FIG. 5 illustrates an example of a portion of a blockchain 500 for use in a distributed medical testing framework, such as the blockchain 602. In some implementations, the blockchain 500 is used to maintain records in one or more databases maintained by the medical test facilitator 102 (or equivalently, medical test facilitator 202). For example, the blockchain 500 can be used to maintain the assessments of genomic tests submitted by clinical experts in the expert DB 206b; to store the results of the evaluations of the expert assessments in the consensus DB blockchain 206c; to store the educational information in the educational information DB 206d; to store clinical outcomes submitted by consumers in the clinical outcome DB 206e; to record the clinical patterns obtained as results of the data mining in the proprietary health DB 206f; or any suitable combination of these. In some implementations, the blockchain 500 is used for financial transactions. For example, the blockchain 500 can store cryptocurrency tokens (specific to the blockchain 500 or public cryptocurrencies, such as Ethereum) that are used to compensate clinical experts for providing assessments of genomic tests, compensate industry participants for providing information about genomic tests, or compensate consumers for clinical outcomes of genomic tests. Additionally or alternatively, the blockchain 500 can store cryptocurrency tokens that are received as payment from consumers for allowing them to access the consensus evaluations of genomic tests from the consensus DB 206c, or from third parties for allowing them to access the clinical outcomes or the clinical patterns from the clinical outcome DB 206e or the proprietary health DB 206f, respectively. Additionally or alternatively, the blockchain 500 can store NFTs that are transferrable to transfer access to medical data, which may be stored on the blockchain 500 itself or external to the blockchain 500.

The blockchain 500 includes one or more blocks, such as blocks 510, 520 and 530, that are linked to one another. Each block includes: a value field, such as value 512, value 522 and value 532 in the blocks 510, 520 and 530, respectively; a previous hash field, such as prev_hash 514, prev_hash 524 and prev_hash 534 in the blocks 510, 520 and 530, respectively; a timestamp field, such as timestamps 516, 526 and 536 in the blocks 510, 520 and 530, respectively; a nonce field, such as nonces 518, 528 and 538 in the blocks 510, 520 and 530, respectively; and a signature field, such as signatures 519, 529 and 539 in the blocks 510, 520 and 530, respectively.

A block, for example, one or more of blocks 510, 520 or 530, corresponds to a transaction in the blockchain 500, and stores records of the transaction. The value field in a block stores the particular transaction value. For example, when the blockchain 500 is used in the expert DB 206b, one or more of the value fields 512, 522 or 532 can be used to store the assessments of genomic tests submitted by the clinical experts. As another example, when the blockchain 500 is used in the educational information DB 206d, one or more of the value fields 512, 522 or 532 can be used to store educational information for particular genomic tests. As another example, when the blockchain 500 is used in the clinical outcome DB 206e, one or more of the value fields 512, 522 or 532 can be used to store information about results of a genomic test provided by a medical provider, such as feedback on the test results, its clinical manifestations for the patient of the medical provider, and relevant data about the patient. As yet another example, when the blockchain 500 is used in the proprietary health DB 206f, one or more of the value fields 512, 522 or 532 can be used to store information about clinical patterns about genomic tests that are obtained by data mining. As yet another example, when the blockchain 500 is used for financial transactions, one or more of the value fields 512, 522 or 532 can be used to store cryptocurrency information.

The blocks in the blockchain 500, e.g., blocks 510, 520 or 530, are linked to one another, forming a chain, using cryptographic hashes. Each block includes the cryptographic hash of the prior block in the blockchain, linking the two. The linked blocks form a chain. For example, as shown, the prev_hash 524 in block 520 includes a cryptographic hash of the contents of the preceding block 510. The prev_hash 524 is computed by hashing one or more, or all, the fields in the block 510, including one or more of value 512, prev_hash 514, timestamp 516, nonce 518 and signature 519. Similarly, prev_hash 534 in block 530 includes a cryptographic hash of the contents of the preceding block 520, for example a cryptographic hash on one or more (or all) of value 522, prev_hash 524, timestamp 526, nonce 528 and signature 529. A cryptographic hash is generated using any suitable hashing mechanism using a hashing algorithm, for example, SHA-512/256 or MD5.

The timestamp field in each block of the blockchain 500, for example, timestamps 516, 526 and 536, denote the time of creation of the respective block, which corresponds to the time of the respective transaction. For example, when the blockchain 500 is used in the expert DB 206b, the timestamp 516 can indicate the time when the block 510 was created in the blockchain 500 to record a transaction in which a clinical expert uploaded his or her assessment about a particular genomic test and associated clinical claims. Similarly, the timestamp 526 can indicate the time when the block 520 was created in the blockchain 500 to record another transaction in which a clinical expert uploaded his or her assessment about a genomic test and associated clinical claims. The genomic tests implicated by the blocks 510 and 520 can be same or different. The assessments for the blocks 510 and 520 can be from the same expert (for example, for different genomic tests) or from different experts (for example, assessments for the same genomic test or different genomic tests).

Each block is cryptographically signed, with the signature for the block included in the signature field in the block. For example, signature fields 519, 529 and 539 include the cryptographic signatures of the blocks 510, 520 and 530 respectively. In some implementations, a cryptographic key of the entity associated with the transaction is used to generate the signature for the respective block. For example, when the blockchain 500 is used in the expert DB 206b, the signature 519 can be generated using the cryptographic key belonging to the clinical expert who uploaded the assessment for the block 510. As another example, when the blockchain 500 is used in the claims DB 206a, the signature 519 can be generated using the cryptographic key belonging to an industry participant that provided information about the particular genomic test (e.g., a claim about the particular genomic test), or the cryptographic key can be associated with a computer system, algorithm, or other analysis source that performed analysis to determine the information. For example, the cryptographic key can be associated with a source (such as a computer system, algorithm, organization, or user) that analyzed consumer feedback data or test result data to determine the information.

The nonce field in each block of the blockchain 500, for example, nonces 518, 528 and 538, includes a random value that is added to a block to strengthen the security of the cryptographic signature operation. A nonce for a block is generated, for example, using a random number generator, when the corresponding block is created. Use of the nonces help to prevent various security attacks, such as replay attacks.

The disclosed and other examples can be implemented as one or more computer program products, for example, one or more modules of computer program instructions encoded on a computer readable medium for execution by, or to control the operation of, data processing apparatus. The computer readable medium can be a machine-readable storage device, a machine-readable storage substrate, a memory device, or a combination of one or more them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, for example, code that constitutes processor firmware, a protocol stack, a database management system, an operating system, or a combination of one or more of them.

A system may encompass all apparatus, devices, and machines for processing data, including by way of example a programmable processor, a computer, or multiple processors or computers. A system can include, in addition to hardware, code that creates an execution environment for the computer program in question, for example, code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (for example, one or more scripts stored in a markup language document), in a single file dedicated to the program in question, or in multiple coordinated files (for example, files that store one or more modules, sub programs, or portions of code). A computer program can be deployed for execution on one computer or on multiple computers that are located at one site or distributed across multiple sites and interconnected by a communications network.

The processes and logic flows described in this document can be performed by one or more programmable processors executing one or more computer programs to perform the functions described herein. The processes and logic flows can also be performed by, and apparatus can also be implemented as, special purpose logic circuitry, for example, an FPGA or an ASIC (application specific integrated circuit).

Processors suitable for the execution of a computer program include, by way of example, both general and special purpose microprocessors, and any one or more processors of any kind of digital computer. Computer readable media suitable for storing computer program instructions and data can include all forms of nonvolatile memory, media and memory devices. The processor and the memory can be supplemented by, or incorporated in, special purpose logic circuitry.

While this document may describe many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination in some cases can be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Only a few examples and implementations are disclosed. Variations, modifications, and enhancements to the described examples and implementations and other implementations can be made based on what is disclosed.

What is claimed is:

1. A system comprising:
a first database that is configured to store assessments of genomic tests and is accessible by clinical experts, wherein a clinical expert is enabled to access the first database upon authorization by an administrator;
a second database that is configured to store evaluations of the assessments, wherein the second database is accessible upon authorization by the administrator;
a third database;
a blockchain database;
one or more processors; and
storage media having stored thereon instructions that, when executed by the one or more processors, cause the one or more processors to perform operations comprising:
receiving an input including information about a particular genomic test;
in response to receiving the information, sending, to a group of the clinical experts, a notification about availability of the information;
receiving, from one or more of the group of the clinical experts, particular assessments of the information;
storing the particular assessments in the first database;
processing the particular assessments by applying one or more functions operating on an aggregate of the particular assessments, the processing including comparing an output of the one or more functions to a preselected threshold;
in response to the processing, determining a result indicating a status of the particular genomic test; and
storing one or more of the result or the information about the particular genomic test in the second database,
wherein the third database is configured to store medical data comprising a result of the particular genomic test administered to a patient, and patient information characterizing the patient, and
wherein the blockchain database is configured to store a non-fungible token corresponding to the medical data, wherein the non-fungible token comprises an identifier of the medical data.

2. The system of claim 1, wherein processing the particular assessments by applying one or more functions on the aggregate of the particular assessments comprises applying a consensus testing mechanism on an aggregate of blockchain transactions that include an identifier of the particular genomic test, and
wherein comparing the output of the one or more functions to the preselected threshold comprises determining whether a number of assessments of the particular genomic test meet a quorum size.

3. The system of claim 1, wherein storing one or more of the result or the information about the particular genomic test in the second database comprises:
adding the result as a transaction in a blockchain stored in the second database, the transaction including an identifier of the particular genomic test and authenticated using a cryptographic identifier corresponding to the administrator.

4. The system of claim 3, further comprising a server that is coupled to the second database and configured to provide the result or the information about the particular genomic test to connected client devices, wherein providing the result or the information about the particular genomic test comprises:
enabling a client device of a consumer to establish a network connection to the server using a blockchain-based browser; and
presenting one or more of the result or the information about the particular genomic test on a user interface of the blockchain-based browser, the user interface shown on the client device.

5. The system of claim 1, wherein the operations comprise storing the information about the particular genomic test as a transaction in a blockchain, wherein the transaction is authenticated using a cryptographic identifier corresponding to (i) an industry participant that provided the information about the particular genomic test or (ii) a source that analyzed consumer feedback data to determine the information.

6. The system of claim 1, further comprising a fourth database storing contextual educational information about the particular genomic test, wherein the contextual educational information is stored as a transaction in a blockchain stored in the fourth database, and wherein the operations further comprise:
storing, with one or more of the result or the information about the particular genomic test stored in the second database, a link to the contextual educational information,
wherein the transaction comprises an identifier of the particular genomic test and is authenticated using a cryptographic identifier corresponding to the administrator.

7. The system of claim 1, wherein the operations comprise:
receiving, from a consumer, a predetermined amount of cryptocurrency tokens; and
in response to receiving the predetermined amount of cryptocurrency tokens, providing the consumer access to at least one of the result or the information about the particular genomic test in the second database.

8. The system of claim 1, wherein the blockchain database comprises a smart contract that, when invoked, is configured to:
determine that an invoker of the smart contract is an owner of the non-fungible token; and
in response to determining that the invoker is the owner of the non-fungible token, provide the medical data to the invoker of the smart contract.

9. The system of claim 1, wherein the blockchain database comprises a smart contract managed by a decentralized autonomous organization,
wherein membership in the decentralized autonomous organization corresponds to ownership of tokens of the blockchain database, and
wherein the smart contract is invocable to alter parameters of one or more other smart contracts of the blockchain database.

10. A method comprising:
receiving an input including information about a particular genomic test;
in response to receiving the information, sending, to a group of clinical experts, a notification about availability of the information;
receiving, from one or more of the group of the clinical experts, particular assessments of the information;
storing the particular assessments in a first database, wherein the first database is configured to store assessments of genomic tests and is accessible by clinical experts;
processing the particular assessments by applying one or more functions operating on an aggregate of the particular assessments, the processing including comparing an output of the one or more functions to a preselected threshold;
in response to the processing, determining a result indicating a status of the particular genomic test;
storing one or more of the result or the information about the particular genomic test in a second database that is configured to store evaluations of the assessments of genomic tests, wherein the second database is accessible upon authorization by an administrator;
receiving, from a consumer, medical data comprising an outcome of the particular genomic test administered to a patient, and patient information characterizing the patient; and
in response to receiving the medical data, providing, to the consumer, a predetermined amount of cryptocurrency, and storing the medical data in a blockchain database.

11. The method of claim 10, wherein storing one or more of the result or the information about the particular genomic test in the second database comprises:
adding the result as a transaction in a blockchain stored in the second database, the transaction including an identifier of the particular genomic test, and authenticated using a cryptographic identifier corresponding to the administrator.

12. The method of claim 10, comprising:
storing a non-fungible token corresponding to the medical data, wherein the non-fungible token comprises an identifier of the medical data.

13. The method of claim 12, comprising storing, in the blockchain database, a smart contract configured to, when invoked:
confirm that an invoker of the smart contract is an owner of the non-fungible token; and
in response to confirming that the invoker is the owner of the non-fungible token, provide the medical data to the invoker of the smart contract.

14. The method of claim 10, wherein processing the particular assessments by applying one or more functions on the aggregate of the particular assessments comprises applying a consensus testing mechanism on an aggregate of blockchain transactions that include an identifier of the particular genomic test, and
wherein comparing the output of the one or more functions to the preselected threshold comprises determining whether a number of assessments of the particular genomic test meet a quorum size.

15. A method comprising:
receiving an input including information about a particular genomic test;
in response to receiving the information, sending, to a group of clinical experts, a notification about availability of the information;
receiving, from one or more of the group of the clinical experts, particular assessments of the information;
storing the particular assessments in a first database, wherein the first database is configured to store assessments of genomic tests and is accessible by clinical experts;
processing the particular assessments by applying one or more functions operating on an aggregate of the particular assessments, the processing including:
comparing an output of the one or more functions to a preselected threshold, wherein the comparison comprises determining whether a number of assessments of the particular genomic test meets a quorum size, and
applying a consensus testing mechanism on an aggregate of blockchain transactions that include an identifier of the particular genomic test;
in response to the processing, determining a result indicating a status of the particular genomic test; and
storing one or more of the result or the information about the particular genomic test in a second database that is configured to store evaluations of the assessments of genomic tests, wherein the second database is accessible upon authorization by an administrator.

16. The method of claim 15, comprising:
storing, in a third database, medical data comprising a result of the particular genomic test administered to a patient, and patient information characterizing the patient; and
storing, in a blockchain database, a non-fungible token corresponding to the medical data, wherein the non-fungible token comprises an identifier of the medical data.

17. A system comprising:
a first database that is configured to store assessments of genomic tests and is accessible by clinical experts, wherein a clinical expert is enabled to access the first database upon authorization by an administrator;

a second database that is configured to store evaluations of the assessments, wherein the second database is accessible upon authorization by the administrator;

a third database configured to store patient data corresponding to particular medical test instances;

a fourth database configured to store analytical information corresponding to the patient data;

one or more processors; and storage media having stored thereon instructions that, when executed by the one or more processors, cause the one or more processors to perform operations comprising:

receiving an input including information about a particular genomic test;

in response to receiving the information, sending, to a group of the clinical experts, a notification about availability of the information;

receiving, from one or more of the group of the clinical experts, particular assessments of the information;

storing the particular assessments in the first database;

processing the particular assessments by applying one or more functions operating on an aggregate of the particular assessments, the processing including comparing an output of the one or more functions to a preselected threshold;

in response to the processing, determining a result indicating a status of the particular genomic test;

storing one or more of the result or the information about the particular genomic test in the second database;

receiving, in the third database, from a consumer, particular patient data corresponding to administration of the particular genomic test on a particular patient;

obtaining aggregate patient data for the particular genomic test by combining the particular patient data with one or more other patient data corresponding to other administrations of the particular genomic test on other patients;

analyzing the aggregate patient data, including determining, using the aggregate patient data, one or more clinical patterns corresponding to the particular genomic test; and storing the one or more clinical patterns in at least one of the first database or the fourth database, wherein storing the one or more clinical patterns in the fourth database includes publishing information about availability of the one or more clinical patterns in the fourth database.

18. The system of claim 17, wherein analyzing the aggregate patient data comprises processing the aggregate patient data using at least one of data mining tools or artificial intelligence-based analytical tools, and wherein the one or more clinical patterns are stored in the fourth database as a transaction in a blockchain, the transaction including an identifier of the particular genomic test and authenticated using a cryptographic identifier corresponding to the administrator.

19. The system of claim 17, wherein the operations comprise:

receiving, from a third party, a predetermined amount of cryptocurrency tokens stored in a blockchain database; and in response to receiving the predetermined amount of cryptocurrency tokens, enabling the third party to access the one or more clinical patterns from the fourth database.

20. A method comprising:

receiving an input including information about a particular genomic test;

in response to receiving the information, sending, to a group of clinical experts, a notification about availability of the information;

receiving, from one or more of the group of the clinical experts, particular assessments of the information;

storing the particular assessments in a first database, wherein the first database is configured to store assessments of genomic tests and is accessible by clinical experts;

processing the particular assessments by applying one or more functions operating on an aggregate of the particular assessments, the processing including comparing an output of the one or more functions to a preselected threshold;

in response to the processing, determining a result indicating a status of the particular genomic test;

storing one or more of the result or the information about the particular genomic test in a second database that is configured to store evaluations of the assessments of genomic tests, wherein the second database is accessible upon authorization by an administrator;

storing, in a third database, medical data comprising a result of the particular genomic test administered to a patient and patient information characterizing the patient; and storing, in a blockchain database, a non-fungible token corresponding to the medical data, wherein the non-fungible token comprises an identifier of the medical data.

21. The method of claim 20, comprising storing, in the blockchain database, a smart contract configured to, when invoked:

confirm that an invoker of the smart contract is an owner of the non-fungible token; and in response to confirming that the invoker is the owner of the non-fungible token, provide the medical data to the invoker of the smart contract.

22. The method of claim 20, wherein the blockchain database comprises a smart contract managed by a decentralized autonomous organization, wherein membership in the decentralized autonomous organization corresponds to ownership of tokens of the blockchain database, and wherein the smart contract is invocable to alter parameters of one or more other smart contracts of the blockchain database.

23. A system comprising:

one or more processors; and memory storing instructions that are configured to, when executed, cause the one or more processors to perform operations comprising:

receiving an input including information about a particular genomic test;

in response to receiving the information, sending, to a group of clinical experts, a notification about availability of the information;

receiving, from one or more of the group of the clinical experts, particular assessments of the information;

storing the particular assessments in a first database, wherein the first database is configured to store assessments of genomic tests and is accessible by clinical experts;

processing the particular assessments by applying one or more functions operating on an aggregate of the particular assessments, the processing including comparing an output of the one or more functions to a preselected threshold;

in response to the processing, determining a result indicating a status of the particular genomic test;

storing one or more of the result or the information about the particular genomic test in a second database that is configured to store evaluations of the assessments of genomic tests, wherein the second database is accessible upon authorization by an administrator;

receiving, from a consumer, medical data comprising an outcome of the particular genomic test administered to a patient, and patient information characterizing the patient; and in response to receiving the medical data, providing, to the consumer, a predetermined amount of cryptocurrency, and storing the medical data in a blockchain database.

24. A system comprising:

one or more processors; and memory storing instructions that are configured to, when executed, cause the one or more processors to perform operations comprising:

receiving an input including information about a particular genomic test;

in response to receiving the information, sending, to a group of clinical experts, a notification about availability of the information;

receiving, from one or more of the group of the clinical experts, particular assessments of the information;

storing the particular assessments in a first database, wherein the first database is configured to store assessments of genomic tests and is accessible by clinical experts;

processing the particular assessments by applying one or more functions operating on an aggregate of the particular assessments, the processing including:

comparing an output of the one or more functions to a preselected threshold, wherein the comparison comprises determining whether a number of assessments of the particular genomic test meets a quorum size, and applying a consensus testing mechanism on an aggregate of blockchain transactions that include an identifier of the particular genomic test;

in response to the processing, determining a result indicating a status of the particular genomic test; and storing one or more of the result or the information about the particular genomic test in a second database that is configured to store evaluations of the assessments of genomic tests, wherein the second database is accessible upon authorization by an administrator.

* * * * *